US012715924B2

(12) United States Patent
Paller et al.

(10) Patent No.: US 12,715,924 B2
(45) Date of Patent: Aug. 25, 2026

(54) METHOD OF TREATING ICHTHYOSIS IN A SUBJECT BY ADMINISTERING AN ANTI-INTERLEUKIN 36 RECEPTOR (IL-36R) BINDING AGENT

(71) Applicant: AnaptysBio, Inc., San Diego, CA (US)

(72) Inventors: Amy Paller, Wilmette, IL (US); Emma Guttman, New York, NY (US); Irina Khanskaya, Morristown, NY (US); Rupal Kalapanda, San Diego, CA (US); Marco Londei, La Jolla, CA (US)

(73) Assignee: ANAPTYSBIO, INC., San Diego, CA (US)

(*) Notice: Subject to any disclaimer, the term of this patent is extended or adjusted under 35 U.S.C. 154(b) by 758 days.

(21) Appl. No.: 18/007,361

(22) PCT Filed: Jul. 30, 2021

(86) PCT No.: PCT/US2021/043907
§ 371 (c)(1),
(2) Date: Jan. 30, 2023

(87) PCT Pub. No.: WO2022/026832
PCT Pub. Date: Feb. 3, 2022

(65) Prior Publication Data

US 2023/0272092 A1 Aug. 31, 2023

Related U.S. Application Data

(60) Provisional application No. 63/058,938, filed on Jul. 30, 2020.

(51) Int. Cl.
*C07K 16/28* (2006.01)
*A61P 17/00* (2006.01)
*G01N 33/68* (2006.01)

(52) U.S. Cl.
CPC .......... *C07K 16/2866* (2013.01); *A61P 17/00* (2018.01); *G01N 33/6869* (2013.01); *C07K 2317/51* (2013.01); *C07K 2317/515* (2013.01); *C07K 2317/565* (2013.01); *C07K 2317/76* (2013.01); *G01N 2333/54* (2013.01); *G01N 2333/7155* (2013.01); *G01N 2800/52* (2013.01)

(58) Field of Classification Search
CPC ............ C07K 16/2866; C07K 2317/51; C07K 2317/515; C07K 2317/565; C07K 2317/76; A61P 17/00; A61P 17/10; G01N 33/6869; G01N 2333/54; G01N 2333/7155; G01N 2800/52; A61K 39/3955
See application file for complete search history.

(56) References Cited

U.S. PATENT DOCUMENTS

| | | | |
|---|---|---|---|
| 9,023,995 B2 | 5/2015 | Brown et al. | |
| 10,526,410 B2 * | 1/2020 | Bowers .............. | C07K 16/2866 |
| 10,550,189 B2 | 2/2020 | Brown et al. | |
| 2020/0087408 A1 | 3/2020 | Bowers et al. | |
| 2022/0073628 A1 * | 3/2022 | Fine .................. | C07K 16/2866 |
| 2023/0011052 A1 | 1/2023 | Guzman et al. | |

FOREIGN PATENT DOCUMENTS

| | | |
|---|---|---|
| CN | 107847590 A | 3/2018 |
| JP | 2018-512157 A | 5/2018 |
| JP | 2023506015 A | 2/2023 |
| WO | 2013074569 A1 | 5/2013 |
| WO | 2016168542 A1 | 10/2016 |
| WO | 2018183173 A1 | 10/2018 |
| WO | 2019177883 A2 | 9/2019 |
| WO | 2019177888 A1 | 9/2019 |
| WO | 2020018503 A2 | 1/2020 |

OTHER PUBLICATIONS

Paul, WE (1993) Fundamental Immunology, 3rd ed. Raven Press, NY, Chap. 9, pp. 292-295.*
Rudikoff, S et al. (1982) Proc. Natl. Acad. Sci. USA, 79:1979-1983 (doi: 10.1073/pnas.79.6.1979).*
Colman, PM (1994) Research in Immunology, Elsevier, NY, 145(1):33-36.*
Bendig M. M. (1995) Methods: A Companion to Methods in Enzymology, 8:83-93.*
Maccallum et al. (Oct. 11, 1996) J. Mol. Biol., 262(5):732-745. (doi: 10.1006/jmbi.1996.0548).*
Casset et al (2003) Biochemical and Biophysical Research Communications, 307:198-205. (doi:10.1016/S0006-291X(03)01131-8).*
Chen et al. (1995) EMBO J., 14(12):2784-2794. (doi: 10.1002/j.1460-2075.1995.tb07278.x).*
Scheffer L, et al. (Nov. 2024) Briefings in Bioinformatics. 25(6):1-10. (https://doi.org/10.1093/bib/bbae537).*
Valdes-Trescano MS, et al. (2023) Molecules. 28(10):3991. pp. 1-7. (https://doi.org/10.3390/molecules28103991).*
Ye C, et al. JMIR Bioinform Biotechnol. Oct. 28, 2022;3(1):e29404. pp. 1-7. (doi: 10.2196/29404).*
Yuan Z-C, et al. (Oct. 2019) Frontiers in Immunology. 10(2532):1-8 (doi: 10.3389/fimmu.2019.02532).*
Todorovic V, et al. (2019) Scientific Reports. 9(9089):1-15. (https://doi.org/10.1038/s41598-019-45626-w).*
Mahil, S.K., et al., “An analysis of IL-36 signature genes and individuals with IL1RL2 knockout mutations validates IL-36 as a psoriasis therapeutic target,” Science Translational Medicine Oct. 11, 2017, vol. 9, Issue 411, 23 pp.
Search Report issued Nov. 7, 2024 by the China Intellectual Property Office in Application No. CN2021800669540, filed Jul. 30, 2021.
International Search Report, dated Oct. 27, 2021, in International Patent Appl. No. PCT/US2021/043907.

(Continued)

*Primary Examiner* — Robert S Landsman
(74) *Attorney, Agent, or Firm* — BakerHostetler

(57) ABSTRACT

The invention relates to methods of treating ichthyosis in a subject with an inhibitor of the interleukin 36 (IL-36) pathway, and methods of selecting a subject for therapy with the IL-36 pathway inhibitor.

14 Claims, 6 Drawing Sheets

Specification includes a Sequence Listing.

(56) References Cited

OTHER PUBLICATIONS

Malik, K., et al., "Ichthyosis molecular fingerprinting shows profound TH17 skewing and a unique barrier genomic signature," Journal of Allergy and Clinical Immunology, vol. 143, No. 2, Feb. 1, 2019, pp. 604-618.

Rudikoff S., et al., "Single amino acid substitution altering antigen-binding specificity," Proceedings of the National Academy of Sciences, National Academy of Sciences, vol. 79, Mar. 1, 1982, pp. 1979-1983.

Dinarello, IL-1 family nomenclature, Nat. Immunol. 11(11): 973, 2010.

Marukian et al., Recent advances in understaF1000Research 2016, 5(F1000 Faculty Rev):1497, pp. 1-9, 2016, https://doi.org/10.12688/f1000research.8584.1.

Marukian et al., Establishing and Validating an Ichthyosis Severity Index, Journal of Investigative Dermatology, 137: 1834-1841, 2017, doi:10.1016/j.jid.2017.04.037.

Paller et al. Therapeutic pipeline for atopic dermatitis: End of the drought?, J Allergy Clin Immunol, 140(3): 633-643, 2017, http://dx.doi.org/10.1016/j.jaci.2017.07.006.

Towne et al., Interleukin (IL)-1F6, IL-1F8, and IL-1F9 Signal through IL-1Rrp2 and IL-1RAcP to Activate the Pathway Leading to NF-kB and MAPKs, The Journal of Biological Chemistry, 279(14), 13677-13688, 2004, DOI 10.1074/jbc.M400117200.

Hwang et al., A review of IL-36: an emerging therapeutic target for inflammatory dermatoses, Journal of Dermatological Treatment, 33 (6): 2711-2722, 2022, DOI: 10.1080/09546634.2022.2067819.

Joosten et al., New developments in the molecular treatment of ichthyosis: review of the literature, Orphanet Journal of Rare Diseases, 17(269): 1-15, 2022, https://doi.org/10.1186/s13023-022-02430-6.

* cited by examiner

FIG. 2B

SEQUENCE LISTING

<160> NUMBER OF SEQ ID NOS: 90

<210> SEQ ID NO 1
<211> LENGTH: 116
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (4)..(4)
<223> OTHER INFORMATION: Xaa1 is leucine (Leu) or phenylalanine (Phe)
<220> FEATURE:
<221> NAME/KEY: MISC_FEATURE
<222> LOCATION: (5)..(5)
<223> OTHER INFORMATION: Xaa2 is valine (Val), methionine (Met), or leucine (Leu)
<220> FEATURE:
<221> NAME/KEY: MISC_FEATURE
<222> LOCATION: (44)..(44)
<223> OTHER INFORMATION: Xaa3 is arginine (Arg) or glycine (Gly)
<220> FEATURE:
<221> NAME/KEY: MISC_FEATURE
<222> LOCATION: (56)..(56)
<223> OTHER INFORMATION: Xaa4 is glycine (Gly), serine (Ser), or alanine (Ala)
<220> FEATURE:
<221> NAME/KEY: MISC_FEATURE
<222> LOCATION: (72)..(72)
<223> OTHER INFORMATION: Xaa5 is arginine (Arg) or alanine (Ala)
<220> FEATURE:
<221> NAME/KEY: MISC_FEATURE
<222> LOCATION: (74)..(74)
<223> OTHER INFORMATION: Xaa6 is threonine (Thr) or lysine (Lys)
<220> FEATURE:
<221> NAME/KEY: MISC_FEATURE
<222> LOCATION: (84)..(84)
<223> OTHER INFORMATION: Xaa7 is serine (Ser) or alanine (Ala)
<220> FEATURE:
<221> NAME/KEY: MISC_FEATURE
<222> LOCATION: (95)..(95)
<223> OTHER INFORMATION: Xaa8 is tyrosine (Tyr) or phenylalanine (Phe)

<400> SEQUENCE: 1

```
Gln Val Gln Xaa Xaa Gln Ser Gly Ala Glu Val Lys Lys Pro Gly Ala
1               5                   10                  15

Ser Val Lys Val Ser Cys Lys Ala Ser Gly Phe Thr Phe Thr Ser Tyr
            20                  25                  30

Asp Ile Asn Trp Val Arg Gln Ala Pro Gly Gln Xaa Leu Glu Trp Met
        35                  40                  45

Gly Trp Ile Tyr Pro Gly Asp Xaa Ser Thr Lys Tyr Asn Glu Lys Phe
    50                  55                  60

Lys Gly Arg Val Thr Ile Thr Xaa Asp Xaa Ser Ala Ser Thr Ala Tyr
65                  70                  75                  80

Met Glu Leu Xaa Ser Leu Arg Ser Glu Asp Thr Ala Val Tyr Xaa Cys
                85                  90                  95

Thr Arg Ser Phe Tyr Thr Met Asp Tyr Trp Gly Gln Gly Thr Thr Val
            100                 105                 110

Thr Val Ser Ser
        115
```

<210> SEQ ID NO 2
<211> LENGTH: 116
<212> TYPE: PRT
<213> ORGANISM: Artificial Sequence
<220> FEATURE:
<223> OTHER INFORMATION: Synthetic Sequence

<400> SEQUENCE: 2

```
Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Ser Tyr
            20                  25                  30

Asp Ile Asn Trp Val Arg Gln Ala Pro Gly Gln Arg Leu Glu Trp Met
        35                  40                  45

Gly Trp Ile Tyr Pro Gly Asp Gly Ser Thr Lys Tyr Asn Glu Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Ser Phe Tyr Thr Met Asp Tyr Trp Gly Gln Gly Thr Thr Val
            100                 105                 110

Thr Val Ser Ser
        115


<210> SEQ ID NO 3
<211> LENGTH: 116
<212> TYPE: PRT
<213> ORGANISM: Artificial Sequence
<220> FEATURE:
<223> OTHER INFORMATION: Synthetic Sequence

<400> SEQUENCE: 3

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Ser Tyr
            20                  25                  30

Asp Ile Asn Trp Val Arg Gln Ala Pro Gly Gln Gly Leu Glu Trp Met
        35                  40                  45

Gly Trp Ile Tyr Pro Gly Asp Gly Ser Thr Lys Tyr Asn Glu Lys Phe
    50                  55                  60

Lys Gly Arg Val Thr Ile Thr Ala Asp Lys Ser Ala Ser Thr Ala Tyr
65                  70                  75                  80

Met Glu Leu Ser Ser Leu Arg Ser Glu Asp Thr Ala Val Tyr Phe Cys
                85                  90                  95

Thr Arg Ser Phe Tyr Thr Met Asp Tyr Trp Gly Gln Gly Thr Thr Val
            100                 105                 110

Thr Val Ser Ser
        115


<210> SEQ ID NO 4
<211> LENGTH: 116
<212> TYPE: PRT
<213> ORGANISM: Artificial Sequence
<220> FEATURE:
<223> OTHER INFORMATION: Synthetic Sequence

<400> SEQUENCE: 4

Gln Val Gln Leu Met Gln Ser Gly Ala Glu Val Lys Lys Pro Gly Ala
1               5                   10                  15

Ser Val Lys Val Ser Cys Lys Ala Ser Gly Phe Thr Phe Thr Ser Tyr
            20                  25                  30

Asp Ile Asn Trp Val Arg Gln Ala Pro Gly Gln Arg Leu Glu Trp Met
        35                  40                  45

Gly Trp Ile Tyr Pro Gly Asp Ser Ser Thr Lys Tyr Asn Glu Lys Phe
```

```
    50                  55                  60

Lys Gly Arg Val Thr Ile Thr Arg Asp Lys Ser Ala Asn Thr Ala Tyr
65                  70                  75                  80

Met Glu Leu Ala Ser Leu Arg Ser Glu Asp Thr Ala Val Tyr Phe Cys
                85                  90                  95

Thr Arg Ser Phe Tyr Thr Met Asp Tyr Trp Gly Gln Gly Thr Thr Val
            100                 105                 110

Thr Val Ser Ser
        115


<210> SEQ ID NO 5
<211> LENGTH: 116
<212> TYPE: PRT
<213> ORGANISM: Artificial Sequence
<220> FEATURE:
<223> OTHER INFORMATION: Synthetic Sequence

<400> SEQUENCE: 5

Gln Val Gln Leu Met Gln Ser Gly Ala Glu Val Lys Lys Pro Gly Ala
1               5                   10                  15

Ser Val Lys Val Ser Cys Lys Ala Ser Gly Phe Thr Phe Thr Ser Tyr
            20                  25                  30

Asp Ile Asn Trp Val Arg Gln Ala Pro Gly Gln Arg Leu Glu Trp Met
        35                  40                  45

Gly Trp Ile Tyr Pro Gly Asp Ala Ser Thr Lys Tyr Asn Glu Lys Phe
    50                  55                  60

Lys Gly Arg Val Thr Ile Thr Arg Asp Lys Ser Ala Asn Thr Ala Tyr
65                  70                  75                  80

Met Glu Leu Ala Ser Leu Arg Ser Glu Asp Thr Ala Val Tyr Phe Cys
                85                  90                  95

Thr Arg Ser Phe Tyr Thr Met Asp Tyr Trp Gly Gln Gly Thr Thr Val
            100                 105                 110

Thr Val Ser Ser
        115


<210> SEQ ID NO 6
<211> LENGTH: 116
<212> TYPE: PRT
<213> ORGANISM: Artificial Sequence
<220> FEATURE:
<223> OTHER INFORMATION: Synthetic Sequence

<400> SEQUENCE: 6

Gln Val Gln Leu Met Gln Ser Gly Ala Glu Val Lys Lys Pro Gly Ala
1               5                   10                  15

Ser Val Lys Val Ser Cys Lys Ala Ser Gly Phe Thr Phe Thr Ser Tyr
            20                  25                  30

Asp Ile Asn Trp Val Arg Gln Ala Pro Gly Gln Arg Leu Glu Trp Met
        35                  40                  45

Gly Trp Ile Tyr Pro Gly Asp Ser Ser Thr Lys Tyr Asn Glu Lys Phe
    50                  55                  60

Lys Gly Arg Val Thr Ile Thr Ala Asp Lys Ser Ala Asn Thr Ala Tyr
65                  70                  75                  80

Met Glu Leu Ala Ser Leu Arg Ser Glu Asp Thr Ala Val Tyr Phe Cys
                85                  90                  95

Thr Arg Ser Phe Tyr Thr Met Asp Tyr Trp Gly Gln Gly Thr Thr Val
            100                 105                 110
```

```
Thr Val Ser Ser
        115


<210> SEQ ID NO 7
<211> LENGTH: 116
<212> TYPE: PRT
<213> ORGANISM: Artificial Sequence
<220> FEATURE:
<223> OTHER INFORMATION: Synthetic Sequence

<400> SEQUENCE: 7

Gln Val Gln Leu Leu Gln Ser Gly Ala Glu Val Lys Lys Pro Gly Ala
1               5                   10                  15

Ser Val Lys Val Ser Cys Lys Ala Ser Gly Phe Thr Phe Thr Ser Tyr
            20                  25                  30

Asp Ile Asn Trp Val Arg Gln Ala Pro Gly Gln Arg Leu Glu Trp Met
        35                  40                  45

Gly Trp Ile Tyr Pro Gly Asp Ser Ser Thr Lys Tyr Asn Glu Lys Phe
    50                  55                  60

Lys Gly Arg Val Thr Ile Thr Arg Asp Lys Ser Ala Asn Thr Ala Tyr
65                  70                  75                  80

Met Glu Leu Ser Ser Leu Arg Ser Glu Asp Thr Ala Val Tyr Phe Cys
                85                  90                  95

Thr Arg Ser Phe Tyr Thr Met Asp Tyr Trp Gly Gln Gly Thr Thr Val
            100                 105                 110

Thr Val Ser Ser
        115


<210> SEQ ID NO 8
<211> LENGTH: 116
<212> TYPE: PRT
<213> ORGANISM: Artificial Sequence
<220> FEATURE:
<223> OTHER INFORMATION: Synthetic Sequence

<400> SEQUENCE: 8

Gln Val Gln Leu Leu Gln Ser Gly Ala Glu Val Lys Lys Pro Gly Ala
1               5                   10                  15

Ser Val Lys Val Ser Cys Lys Ala Ser Gly Phe Thr Phe Thr Ser Tyr
            20                  25                  30

Asp Ile Asn Trp Val Arg Gln Ala Pro Gly Gln Arg Leu Glu Trp Met
        35                  40                  45

Gly Trp Ile Tyr Pro Gly Asp Ser Ser Thr Lys Tyr Asn Glu Lys Phe
    50                  55                  60

Lys Gly Arg Val Thr Ile Thr Ala Asp Lys Ser Ala Asn Thr Ala Tyr
65                  70                  75                  80

Met Glu Leu Ala Ser Leu Arg Ser Glu Asp Thr Ala Val Tyr Phe Cys
                85                  90                  95

Thr Arg Ser Phe Tyr Thr Met Asp Tyr Trp Gly Gln Gly Thr Thr Val
            100                 105                 110

Thr Val Ser Ser
        115


<210> SEQ ID NO 9
<211> LENGTH: 116
<212> TYPE: PRT
<213> ORGANISM: Artificial Sequence
<220> FEATURE:
<223> OTHER INFORMATION: Synthetic Sequence
```

<400> SEQUENCE: 9

```
Gln Val Gln Leu Leu Gln Ser Gly Ala Glu Val Lys Lys Pro Gly Ala
1               5                   10                  15

Ser Val Lys Val Ser Cys Lys Ala Ser Gly Phe Thr Phe Thr Ser Tyr
            20                  25                  30

Asp Ile Asn Trp Val Arg Gln Ala Pro Gly Gln Arg Leu Glu Trp Met
        35                  40                  45

Gly Trp Ile Tyr Pro Gly Asp Ala Ser Thr Lys Tyr Asn Glu Lys Phe
    50                  55                  60

Lys Gly Arg Val Thr Ile Thr Arg Asp Lys Ser Ala Asn Thr Ala Tyr
65                  70                  75                  80

Met Glu Leu Ala Ser Leu Arg Ser Glu Asp Thr Ala Val Tyr Phe Cys
                85                  90                  95

Thr Arg Ser Phe Tyr Thr Met Asp Tyr Trp Gly Gln Gly Thr Thr Val
            100                 105                 110

Thr Val Ser Ser
        115
```

<210> SEQ ID NO 10
<211> LENGTH: 116
<212> TYPE: PRT
<213> ORGANISM: Artificial Sequence
<220> FEATURE:
<223> OTHER INFORMATION: Synthetic Sequence

<400> SEQUENCE: 10

```
Gln Val Gln Leu Leu Gln Ser Gly Ala Glu Val Lys Lys Pro Gly Ala
1               5                   10                  15

Ser Val Lys Val Ser Cys Lys Ala Ser Gly Phe Thr Phe Thr Ser Tyr
            20                  25                  30

Asp Ile Asn Trp Val Arg Gln Ala Pro Gly Gln Arg Leu Glu Trp Met
        35                  40                  45

Gly Trp Ile Tyr Pro Gly Asp Ser Ser Thr Lys Tyr Asn Glu Lys Phe
    50                  55                  60

Lys Gly Arg Val Thr Ile Thr Arg Asp Lys Ser Ala Asn Thr Ala Tyr
65                  70                  75                  80

Met Glu Leu Ala Ser Leu Arg Ser Glu Asp Thr Ala Val Tyr Phe Cys
                85                  90                  95

Thr Arg Ser Phe Tyr Thr Met Asp Tyr Trp Gly Gln Gly Thr Thr Val
            100                 105                 110

Thr Val Ser Ser
        115
```

<210> SEQ ID NO 11
<211> LENGTH: 116
<212> TYPE: PRT
<213> ORGANISM: Artificial Sequence
<220> FEATURE:
<223> OTHER INFORMATION: Synthetic Sequence

<400> SEQUENCE: 11

```
Gln Val Gln Phe Leu Gln Ser Gly Ala Glu Val Lys Lys Pro Gly Ala
1               5                   10                  15

Ser Val Lys Val Ser Cys Lys Ala Ser Gly Phe Thr Phe Thr Ser Tyr
            20                  25                  30

Asp Ile Asn Trp Val Arg Gln Ala Pro Gly Gln Arg Leu Glu Trp Met
        35                  40                  45
```

```
Gly Trp Ile Tyr Pro Gly Asp Ser Ser Thr Lys Tyr Asn Glu Lys Phe
    50                  55                  60

Lys Gly Arg Val Thr Ile Thr Ala Asp Lys Ser Ala Asn Thr Ala Tyr
65                  70                  75                  80

Met Glu Leu Ser Ser Leu Arg Ser Glu Asp Thr Ala Val Tyr Phe Cys
                85                  90                  95

Thr Arg Ser Phe Tyr Thr Met Asp Tyr Trp Gly Gln Gly Thr Thr Val
            100                 105                 110

Thr Val Ser Ser
        115


<210> SEQ ID NO 12
<211> LENGTH: 116
<212> TYPE: PRT
<213> ORGANISM: Artificial Sequence
<220> FEATURE:
<223> OTHER INFORMATION: Synthetic Sequence

<400> SEQUENCE: 12

Gln Val Gln Phe Val Gln Ser Gly Ala Glu Val Lys Lys Pro Gly Ala
1               5                   10                  15

Ser Val Lys Val Ser Cys Lys Ala Ser Gly Phe Thr Phe Thr Ser Tyr
            20                  25                  30

Asp Ile Asn Trp Val Arg Gln Ala Pro Gly Gln Arg Leu Glu Trp Met
        35                  40                  45

Gly Trp Ile Tyr Pro Gly Asp Ser Ser Thr Lys Tyr Asn Glu Lys Phe
    50                  55                  60

Lys Gly Arg Val Thr Ile Thr Arg Asp Lys Ser Ala Asn Thr Ala Tyr
65                  70                  75                  80

Met Glu Leu Ser Ser Leu Arg Ser Glu Asp Thr Ala Val Tyr Phe Cys
                85                  90                  95

Thr Arg Ser Phe Tyr Thr Met Asp Tyr Trp Gly Gln Gly Thr Thr Val
            100                 105                 110

Thr Val Ser Ser
        115


<210> SEQ ID NO 13
<211> LENGTH: 116
<212> TYPE: PRT
<213> ORGANISM: Artificial Sequence
<220> FEATURE:
<223> OTHER INFORMATION: Synthetic Sequence

<400> SEQUENCE: 13

Gln Val Gln Phe Val Gln Ser Gly Ala Glu Val Lys Lys Pro Gly Ala
1               5                   10                  15

Ser Val Lys Val Ser Cys Lys Ala Ser Gly Phe Thr Phe Thr Ser Tyr
            20                  25                  30

Asp Ile Asn Trp Val Arg Gln Ala Pro Gly Gln Arg Leu Glu Trp Met
        35                  40                  45

Gly Trp Ile Tyr Pro Gly Asp Ser Ser Thr Lys Tyr Asn Glu Lys Phe
    50                  55                  60

Lys Gly Arg Val Thr Ile Thr Ala Asp Lys Ser Ala Asn Thr Ala Tyr
65                  70                  75                  80

Met Glu Leu Ser Ser Leu Arg Ser Glu Asp Thr Ala Val Tyr Phe Cys
                85                  90                  95

Thr Arg Ser Phe Tyr Thr Met Asp Tyr Trp Gly Gln Gly Thr Thr Val
            100                 105                 110
```

```
Thr Val Ser Ser
        115


<210> SEQ ID NO 14
<211> LENGTH: 116
<212> TYPE: PRT
<213> ORGANISM: Artificial Sequence
<220> FEATURE:
<223> OTHER INFORMATION: Synthetic Sequence

<400> SEQUENCE: 14

Gln Val Gln Leu Leu Gln Ser Gly Ala Glu Val Lys Lys Pro Gly Ala
1               5                   10                  15

Ser Val Lys Val Ser Cys Lys Ala Ser Gly Phe Thr Phe Thr Ser Tyr
            20                  25                  30

Asp Ile Asn Trp Val Arg Gln Ala Pro Gly Gln Arg Leu Glu Trp Met
        35                  40                  45

Gly Trp Ile Tyr Pro Gly Asp Ser Ser Thr Lys Tyr Asn Glu Lys Phe
    50                  55                  60

Lys Gly Arg Val Thr Ile Thr Arg Asp Lys Ser Ala Asn Thr Ala Tyr
65                  70                  75                  80

Met Glu Leu Ser Ser Leu Arg Ser Glu Asp Thr Ala Val Tyr Tyr Cys
                85                  90                  95

Thr Arg Ser Phe Tyr Thr Met Asp Tyr Trp Gly Gln Gly Thr Thr Val
            100                 105                 110

Thr Val Ser Ser
        115


<210> SEQ ID NO 15
<211> LENGTH: 120
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (33)..(33)
<223> OTHER INFORMATION: Xaa1 is tryptophan (Trp) or tyrosine (Tyr)
<220> FEATURE:
<221> NAME/KEY: MISC_FEATURE
<222> LOCATION: (35)..(35)
<223> OTHER INFORMATION: Xaa2 is histidine (His), asparagine (Asn), or
      tyrosine (Tyr)
<220> FEATURE:
<221> NAME/KEY: MISC_FEATURE
<222> LOCATION: (42)..(42)
<223> OTHER INFORMATION: Xaa3 is glycine (Gly) or arginine (Arg)
<220> FEATURE:
<221> NAME/KEY: MISC_FEATURE
<222> LOCATION: (52)..(52)
<223> OTHER INFORMATION: Xaa4 is aspartic acid (Asp), glutamic acid
      (Glu), or histidine (His)
<220> FEATURE:
<221> NAME/KEY: MISC_FEATURE
<222> LOCATION: (54)..(54)
<223> OTHER INFORMATION: Xaa5 is serine (Ser), threonine (Thr), or
      tyrosine (Tyr)
<220> FEATURE:
<221> NAME/KEY: MISC_FEATURE
<222> LOCATION: (55)..(55)
<223> OTHER INFORMATION: Xaa6 is asparagine (Asn) or glycine (Gly)
<220> FEATURE:
<221> NAME/KEY: MISC_FEATURE
<222> LOCATION: (56)..(56)
<223> OTHER INFORMATION: Xaa7 is serine (Ser), alanine (Ala), or
      aspartic acid (Asp)

<400> SEQUENCE: 15
```

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Xaa Met Xaa Trp Val Arg Gln Ala Pro Xaa Gln Gly Leu Glu Trp Met
        35                  40                  45

Gly Met Phe Xaa Pro Xaa Xaa Xaa Val Thr Arg Leu Asn Gln Lys Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Thr Thr Ser Met Ile Ile Gly Gly Phe Ala Tyr Trp Gly Gln
            100                 105                 110

Gly Thr Leu Val Thr Val Ser Ser
        115                 120


<210> SEQ ID NO 16
<211> LENGTH: 120
<212> TYPE: PRT
<213> ORGANISM: Artificial Sequence
<220> FEATURE:
<223> OTHER INFORMATION: Synthetic Sequence

<400> SEQUENCE: 16

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met His Trp Val Arg Gln Ala Pro Gly Gln Gly Leu Glu Trp Met
        35                  40                  45

Gly Met Phe Asp Pro Ser Asn Ser Val Thr Arg Leu Asn Gln Lys Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Thr Thr Ser Met Ile Ile Gly Gly Phe Ala Tyr Trp Gly Gln
            100                 105                 110

Gly Thr Leu Val Thr Val Ser Ser
        115                 120


<210> SEQ ID NO 17
<211> LENGTH: 120
<212> TYPE: PRT
<213> ORGANISM: Artificial Sequence
<220> FEATURE:
<223> OTHER INFORMATION: Synthetic Sequence

<400> SEQUENCE: 17

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met His Trp Val Arg Gln Ala Pro Gly Gln Gly Leu Glu Trp Met
        35                  40                  45

Gly Met Phe Glu Pro Ser Asn Ala Val Thr Arg Leu Asn Gln Lys Phe
```

```
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Thr Thr Ser Met Ile Ile Gly Gly Phe Ala Tyr Trp Gly Gln
            100                 105                 110

Gly Thr Leu Val Thr Val Ser Ser
        115                 120


<210> SEQ ID NO 18
<211> LENGTH: 120
<212> TYPE: PRT
<213> ORGANISM: Artificial Sequence
<220> FEATURE:
<223> OTHER INFORMATION: Synthetic Sequence

<400> SEQUENCE: 18

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met Asn Trp Val Arg Gln Ala Pro Arg Gln Gly Leu Glu Trp Met
        35                  40                  45

Gly Met Phe Glu Pro Ser Asn Ala Val Thr Arg Leu Asn Gln Lys Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Thr Thr Ser Met Ile Ile Gly Gly Phe Ala Tyr Trp Gly Gln
            100                 105                 110

Gly Thr Leu Val Thr Val Ser Ser
        115                 120


<210> SEQ ID NO 19
<211> LENGTH: 120
<212> TYPE: PRT
<213> ORGANISM: Artificial Sequence
<220> FEATURE:
<223> OTHER INFORMATION: Synthetic Sequence

<400> SEQUENCE: 19

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met Tyr Trp Val Arg Gln Ala Pro Arg Gln Gly Leu Glu Trp Met
        35                  40                  45

Gly Met Phe His Pro Ser Asn Ala Val Thr Arg Leu Asn Gln Lys Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Thr Thr Ser Met Ile Ile Gly Gly Phe Ala Tyr Trp Gly Gln
            100                 105                 110
```

```
Gly Thr Leu Val Thr Val Ser Ser
        115                 120


<210> SEQ ID NO 20
<211> LENGTH: 120
<212> TYPE: PRT
<213> ORGANISM: Artificial Sequence
<220> FEATURE:
<223> OTHER INFORMATION: Synthetic Sequence

<400> SEQUENCE: 20

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met Asn Trp Val Arg Gln Ala Pro Arg Gln Gly Leu Glu Trp Met
        35                  40                  45

Gly Met Phe His Pro Ser Asn Ala Val Thr Arg Leu Asn Gln Lys Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Thr Thr Ser Met Ile Ile Gly Gly Phe Ala Tyr Trp Gly Gln
            100                 105                 110

Gly Thr Leu Val Thr Val Ser Ser
        115                 120


<210> SEQ ID NO 21
<211> LENGTH: 120
<212> TYPE: PRT
<213> ORGANISM: Artificial Sequence
<220> FEATURE:
<223> OTHER INFORMATION: Synthetic Sequence

<400> SEQUENCE: 21

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Asn Trp Val Arg Gln Ala Pro Arg Gln Gly Leu Glu Trp Met
        35                  40                  45

Gly Met Phe His Pro Thr Gly Asp Val Thr Arg Leu Asn Gln Lys Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Thr Thr Ser Met Ile Ile Gly Gly Phe Ala Tyr Trp Gly Gln
            100                 105                 110

Gly Thr Leu Val Thr Val Ser Ser
        115                 120


<210> SEQ ID NO 22
<211> LENGTH: 120
<212> TYPE: PRT
<213> ORGANISM: Artificial Sequence
<220> FEATURE:
<223> OTHER INFORMATION: Synthetic Sequence
```

<400> SEQUENCE: 22

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Asn Tyr
20 25 30

Trp Met Asn Trp Val Arg Gln Ala Pro Arg Gln Gly Leu Glu Trp Met
35 40 45

Gly Met Phe His Pro Thr Gly Asp Val Thr Arg Leu Asn Gln Lys Phe
50 55 60

Lys Asp Arg Val Thr Met Thr Arg Asp Thr Ser Thr Ser Thr Val Tyr
65 70 75 80

Met Glu Leu Ser Ser Leu Arg Ser Glu Asp Thr Ala Val Tyr Tyr Cys
85 90 95

Ala Arg Thr Thr Ser Met Ile Ile Gly Gly Phe Ala Tyr Trp Gly Gln
100 105 110

Gly Thr Leu Val Thr Val Ser Ser
115 120

<210> SEQ ID NO 23
<211> LENGTH: 120
<212> TYPE: PRT
<213> ORGANISM: Artificial Sequence
<220> FEATURE:
<223> OTHER INFORMATION: Synthetic Sequence

<400> SEQUENCE: 23

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Asn Tyr
20 25 30

Tyr Met Asn Trp Val Arg Gln Ala Pro Arg Gln Gly Leu Glu Trp Met
35 40 45

Gly Met Phe His Pro Tyr Gly Asp Val Thr Arg Leu Asn Gln Lys Phe
50 55 60

Lys Asp Arg Val Thr Met Thr Arg Asp Thr Ser Thr Ser Thr Val Tyr
65 70 75 80

Met Glu Leu Ser Ser Leu Arg Ser Glu Asp Thr Ala Val Tyr Tyr Cys
85 90 95

Ala Arg Thr Thr Ser Met Ile Ile Gly Gly Phe Ala Tyr Trp Gly Gln
100 105 110

Gly Thr Leu Val Thr Val Ser Ser
115 120

<210> SEQ ID NO 24
<211> LENGTH: 120
<212> TYPE: PRT
<213> ORGANISM: Artificial Sequence
<220> FEATURE:
<223> OTHER INFORMATION: Synthetic Sequence

<400> SEQUENCE: 24

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Asn Tyr
20 25 30

Trp Met Asn Trp Val Arg Gln Ala Pro Arg Gln Gly Leu Glu Trp Met
35 40 45

```
Gly Met Phe His Pro Tyr Gly Asp Val Thr Arg Leu Asn Gln Lys Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Thr Thr Ser Met Ile Ile Gly Gly Phe Ala Tyr Trp Gly Gln
            100                 105                 110

Gly Thr Leu Val Thr Val Ser Ser
        115                 120
```

```
<210> SEQ ID NO 25
<211> LENGTH: 117
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: Xaa1 is glutamine (Gln) or aspartic acid (Asp)
<220> FEATURE:
<221> NAME/KEY: MISC_FEATURE
<222> LOCATION: (4)..(4)
<223> OTHER INFORMATION: Xaa2 is leucine (Leu) or phenylalanine (Phe)
<220> FEATURE:
<221> NAME/KEY: MISC_FEATURE
<222> LOCATION: (25)..(25)
<223> OTHER INFORMATION: Xaa3 is threonine (Thr) or serine (Ser)
<220> FEATURE:
<221> NAME/KEY: MISC_FEATURE
<222> LOCATION: (41)..(41)
<223> OTHER INFORMATION: Xaa4 is proline (Pro) or phenylalanine (Phe)
<220> FEATURE:
<221> NAME/KEY: MISC_FEATURE
<222> LOCATION: (44)..(44)
<223> OTHER INFORMATION: Xaa5 is lysine (Lys) or asparagine (Asn)
<220> FEATURE:
<221> NAME/KEY: MISC_FEATURE
<222> LOCATION: (45)..(45)
<223> OTHER INFORMATION: Xaa6 is glycine (Gly) or lysine (Lys)
<220> FEATURE:
<221> NAME/KEY: MISC_FEATURE
<222> LOCATION: (71)..(71)
<223> OTHER INFORMATION: Xaa7 is serine (Ser) or threonine (Thr)
<220> FEATURE:
<221> NAME/KEY: MISC_FEATURE
<222> LOCATION: (72)..(72)
<223> OTHER INFORMATION: Xaa8 is valine (Val) or arginine (Arg)
<220> FEATURE:
<221> NAME/KEY: MISC_FEATURE
<222> LOCATION: (95)..(95)
<223> OTHER INFORMATION: Xaa9 is tyrosine (Tyr) or phenylalanine (Phe)

<400> SEQUENCE: 25

Xaa Val Gln Xaa Gln Glu Ser Gly Pro Gly Leu Val Lys Pro Ser Gln
1               5                   10                  15

Thr Leu Ser Leu Thr Cys Thr Val Xaa Gly Tyr Ser Ile Thr Ser Asp
            20                  25                  30

Phe Ala Trp Asn Trp Ile Arg Gln Xaa Pro Gly Xaa Xaa Leu Glu Trp
        35                  40                  45

Ile Gly Tyr Ile Ser Tyr Ser Gly Asp Thr Asn Tyr Asn Pro Ser Leu
    50                  55                  60

Lys Ser Arg Val Thr Ile Xaa Xaa Asp Thr Ser Lys Asn Gln Phe Ser
65                  70                  75                  80

Leu Lys Leu Ser Ser Val Thr Ala Ala Asp Thr Ala Val Tyr Xaa Cys
                85                  90                  95
```

```
Ala Ile Arg Gly Pro Tyr Ser Phe Thr Tyr Trp Gly Gln Gly Thr Leu
            100                 105                 110

Val Thr Val Ser Ser
        115


<210> SEQ ID NO 26
<211> LENGTH: 117
<212> TYPE: PRT
<213> ORGANISM: Artificial Sequence
<220> FEATURE:
<223> OTHER INFORMATION: Synthetic Sequence

<400> SEQUENCE: 26

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
            20                  25                  30

Phe Ala Trp Asn Trp Ile Arg Gln Pro Pro Gly Lys Gly Leu Glu Trp
        35                  40                  45

Ile Gly Tyr Ile Ser Tyr Ser Gly Asp Thr Asn Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Ile Arg Gly Pro Tyr Ser Phe Thr Tyr Trp Gly Gln Gly Thr Leu
            100                 105                 110

Val Thr Val Ser Ser
        115


<210> SEQ ID NO 27
<211> LENGTH: 117
<212> TYPE: PRT
<213> ORGANISM: Artificial Sequence
<220> FEATURE:
<223> OTHER INFORMATION: Synthetic Sequence

<400> SEQUENCE: 27

Gln Val Gln Phe Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
            20                  25                  30

Phe Ala Trp Asn Trp Ile Arg Gln Pro Pro Gly Lys Gly Leu Glu Trp
        35                  40                  45

Ile Gly Tyr Ile Ser Tyr Ser Gly Asp Thr Asn Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Phe Cys
                85                  90                  95

Ala Ile Arg Gly Pro Tyr Ser Phe Thr Tyr Trp Gly Gln Gly Thr Leu
            100                 105                 110

Val Thr Val Ser Ser
        115


<210> SEQ ID NO 28
<211> LENGTH: 117
<212> TYPE: PRT
<213> ORGANISM: Artificial Sequence
```

```
<220> FEATURE:
<223> OTHER INFORMATION: Synthetic Sequence

<400> SEQUENCE: 28

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
            20                  25                  30

Phe Ala Trp Asn Trp Ile Arg Gln Phe Pro Gly Asn Lys Leu Glu Trp
        35                  40                  45

Ile Gly Tyr Ile Ser Tyr Ser Gly Asp Thr Asn Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Ile Arg Gly Pro Tyr Ser Phe Thr Tyr Trp Gly Gln Gly Thr Leu
            100                 105                 110

Val Thr Val Ser Ser
        115


<210> SEQ ID NO 29
<211> LENGTH: 117
<212> TYPE: PRT
<213> ORGANISM: Artificial Sequence
<220> FEATURE:
<223> OTHER INFORMATION: Synthetic Sequence

<400> SEQUENCE: 29

Gln Val Gln Phe Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
            20                  25                  30

Phe Ala Trp Asn Trp Ile Arg Gln Pro Pro Gly Asn Lys Leu Glu Trp
        35                  40                  45

Ile Gly Tyr Ile Ser Tyr Ser Gly Asp Thr Asn Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Phe Cys
                85                  90                  95

Ala Ile Arg Gly Pro Tyr Ser Phe Thr Tyr Trp Gly Gln Gly Thr Leu
            100                 105                 110

Val Thr Val Ser Ser
        115


<210> SEQ ID NO 30
<211> LENGTH: 117
<212> TYPE: PRT
<213> ORGANISM: Artificial Sequence
<220> FEATURE:
<223> OTHER INFORMATION: Synthetic Sequence

<400> SEQUENCE: 30

Gln Val Gln Phe Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
            20                  25                  30
```

```
Phe Ala Trp Asn Trp Ile Arg Gln Phe Pro Gly Lys Gly Leu Glu Trp
        35                  40                  45

Ile Gly Tyr Ile Ser Tyr Ser Gly Asp Thr Asn Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Phe Cys
                85                  90                  95

Ala Ile Arg Gly Pro Tyr Ser Phe Thr Tyr Trp Gly Gln Gly Thr Leu
            100                 105                 110

Val Thr Val Ser Ser
        115


<210> SEQ ID NO 31
<211> LENGTH: 117
<212> TYPE: PRT
<213> ORGANISM: Artificial Sequence
<220> FEATURE:
<223> OTHER INFORMATION: Synthetic Sequence

<400> SEQUENCE: 31

Gln Val Gln Phe Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
            20                  25                  30

Phe Ala Trp Asn Trp Ile Arg Gln Phe Pro Gly Asn Lys Leu Glu Trp
        35                  40                  45

Ile Gly Tyr Ile Ser Tyr Ser Gly Asp Thr Asn Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Phe Cys
                85                  90                  95

Ala Ile Arg Gly Pro Tyr Ser Phe Thr Tyr Trp Gly Gln Gly Thr Leu
            100                 105                 110

Val Thr Val Ser Ser
        115


<210> SEQ ID NO 32
<211> LENGTH: 117
<212> TYPE: PRT
<213> ORGANISM: Artificial Sequence
<220> FEATURE:
<223> OTHER INFORMATION: Synthetic Sequence

<400> SEQUENCE: 32

Asp Val Gln Phe Gln Glu Ser Gly Pro Gly Leu Val Lys Pro Ser Gln
1               5                   10                  15

Thr Leu Ser Leu Thr Cys Thr Val Thr Gly Tyr Ser Ile Thr Ser Asp
            20                  25                  30

Phe Ala Trp Asn Trp Ile Arg Gln Pro Pro Gly Lys Gly Leu Glu Trp
        35                  40                  45

Ile Gly Tyr Ile Ser Tyr Ser Gly Asp Thr Asn Tyr Asn Pro Ser Leu
    50                  55                  60

Lys Ser Arg Val Thr Ile Thr Arg Asp Thr Ser Lys Asn Gln Phe Ser
65                  70                  75                  80

Leu Lys Leu Ser Ser Val Thr Ala Ala Asp Thr Ala Thr Tyr Phe Cys
                85                  90                  95
```

```
Ala Ile Arg Gly Pro Tyr Ser Phe Thr Tyr Trp Gly Gln Gly Thr Leu
            100                 105                 110

Val Thr Val Ser Ser
        115


<210> SEQ ID NO 33
<211> LENGTH: 116
<212> TYPE: PRT
<213> ORGANISM: Artificial Sequence
<220> FEATURE:
<223> OTHER INFORMATION: Synthetic Sequence

<400> SEQUENCE: 33

Gln Val Gln Leu Gln Gln Ser Gly Pro Glu Leu Val Lys Pro Gly Ala
1               5                   10                  15

Leu Val Lys Ile Ser Cys Lys Ala Ser Gly Phe Thr Phe Thr Ser Tyr
            20                  25                  30

Asp Ile Asn Trp Val Arg Gln Arg Pro Gly Gln Gly Leu Glu Trp Ile
        35                  40                  45

Gly Trp Ile Tyr Pro Gly Asp Gly Ser Thr Lys Tyr Asn Glu Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asn Ser Ala Val Tyr Phe Cys
                85                  90                  95

Thr Arg Ser Phe Tyr Thr Met Asp Tyr Trp Gly Gln Gly Thr Ser Val
            100                 105                 110

Thr Val Ser Ser
        115


<210> SEQ ID NO 34
<211> LENGTH: 120
<212> TYPE: PRT
<213> ORGANISM: Artificial Sequence
<220> FEATURE:
<223> OTHER INFORMATION: Synthetic Sequence

<400> SEQUENCE: 34

Gln Val Gln Leu Gln Gln Ser Gly Pro Glu Leu Val Arg Pro Gly Ala
1               5                   10                  15

Ser Val Arg Met Ser Cys Lys Ala Ser Asp Tyr Thr Phe Thr Asn Tyr
            20                  25                  30

Trp Met His Trp Val Lys Gln Arg Pro Gly Gln Gly Leu Glu Trp Ile
        35                  40                  45

Gly Met Phe Asp Pro Ser Asn Ser Val Thr Arg Leu Asn Gln Lys Phe
    50                  55                  60

Lys Asp Lys Ala Thr Leu Asn Val Asp Lys Ser Ser Asn Thr Ala Tyr
65                  70                  75                  80

Ile Gln Phe Ser Ser Leu Thr Phe Glu Asp Ser Ala Val Tyr Tyr Cys
                85                  90                  95

Ala Arg Thr Thr Ser Met Ile Ile Gly Gly Phe Ala Tyr Trp Gly Gln
            100                 105                 110

Gly Thr Leu Val Thr Val Ser Ser
        115                 120


<210> SEQ ID NO 35
<211> LENGTH: 117
<212> TYPE: PRT
```

```
<213> ORGANISM: Artificial Sequence
<220> FEATURE:
<223> OTHER INFORMATION: Synthetic Sequence

<400> SEQUENCE: 35

Asp Val Gln Phe Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Phe Ala Trp Asn Trp Ile Arg Gln Phe Pro Gly Asn Lys Leu Glu Trp
        35                  40                  45

Met Gly Tyr Ile Ser Tyr Ser Gly Asp Thr Asn Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Phe Cys
                85                  90                  95

Ala Ile Arg Gly Pro Tyr Ser Phe Thr Tyr Trp Gly Pro Gly Thr Leu
            100                 105                 110

Val Thr Val Ser Ser
        115


<210> SEQ ID NO 36
<211> LENGTH: 112
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (34)..(34)
<223> OTHER INFORMATION: Xaa1 is glycine (Gly) or alanine (Ala)
<220> FEATURE:
<221> NAME/KEY: MISC_FEATURE
<222> LOCATION: (41)..(41)
<223> OTHER INFORMATION: Xaa2 is phenylalanine (Phe) or tyrosine (Tyr)
<220> FEATURE:
<221> NAME/KEY: MISC_FEATURE
<222> LOCATION: (54)..(54)
<223> OTHER INFORMATION: Xaa3 is tyrosine (Tyr) or serine (Ser)

<400> SEQUENCE: 36

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Xaa Asn Thr Tyr Leu Tyr Trp Xaa Leu Gln Lys Pro Gly Gln Ser
        35                  40                  45

Pro Gln Leu Leu Ile Xaa Arg Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Gln Gly Thr Lys Leu Glu Ile Lys
            100                 105                 110


<210> SEQ ID NO 37
<211> LENGTH: 112
<212> TYPE: PRT
<213> ORGANISM: Artificial Sequence
<220> FEATURE:
```

<223> OTHER INFORMATION: Synthetic Sequence

<400> SEQUENCE: 37

Asp Ile Val Met Thr Gln Ser Pro Leu Ser Leu Pro Val Thr Pro Gly
1 5 10 15

Glu Pro Ala Ser Ile Ser Cys Arg Ser Ser Lys Ser Leu Leu His Ser
20 25 30

Asn Gly Asn Thr Tyr Leu Tyr Trp Tyr Leu Gln Lys Pro Gly Gln Ser
35 40 45

Pro Gln Leu Leu Ile Tyr Arg Met Ser Asn Leu Ala Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Met Gln His
85 90 95

Leu Glu Tyr Pro Phe Thr Phe Gly Gln Gly Thr Lys Leu Glu Ile Lys
100 105 110

<210> SEQ ID NO 38
<211> LENGTH: 112
<212> TYPE: PRT
<213> ORGANISM: Artificial Sequence
<220> FEATURE:
<223> OTHER INFORMATION: Synthetic Sequence

<400> SEQUENCE: 38

Asp Ile Val Met Thr Gln Ser Pro Leu Ser Leu Pro Val Thr Pro Gly
1 5 10 15

Glu Pro Ala Ser Ile Ser Cys Arg Ser Ser Lys Ser Leu Leu His Ser
20 25 30

Asn Gly Asn Thr Tyr Leu Tyr Trp Phe Leu Gln Lys Pro Gly Gln Ser
35 40 45

Pro Gln Leu Leu Ile Ser Arg Met Ser Asn Leu Ala Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Met Gln His
85 90 95

Leu Glu Tyr Pro Phe Thr Phe Gly Gln Gly Thr Lys Leu Glu Ile Lys
100 105 110

<210> SEQ ID NO 39
<211> LENGTH: 112
<212> TYPE: PRT
<213> ORGANISM: Artificial Sequence
<220> FEATURE:
<223> OTHER INFORMATION: Synthetic Sequence

<400> SEQUENCE: 39

Asp Ile Val Met Thr Gln Ser Pro Leu Ser Leu Pro Val Thr Pro Gly
1 5 10 15

Glu Pro Ala Ser Ile Ser Cys Arg Ser Ser Lys Ser Leu Leu His Ser
20 25 30

Asn Ala Asn Thr Tyr Leu Tyr Trp Phe Leu Gln Lys Pro Gly Gln Ser
35 40 45

Pro Gln Leu Leu Ile Ser Arg Met Ser Asn Leu Ala Ser Gly Val Pro
50 55 60

Asp Arg Phe Ser Gly Ser Gly Ser Gly Thr Asp Phe Thr Leu Lys Ile

```
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Gln Gly Thr Lys Leu Glu Ile Lys
            100                 105                 110


<210> SEQ ID NO 40
<211> LENGTH: 112
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (32)..(32)
<223> OTHER INFORMATION: Xaa1 is serine (Ser) or arginine (Arg)
<220> FEATURE:
<221> NAME/KEY: MISC_FEATURE
<222> LOCATION: (34)..(34)
<223> OTHER INFORMATION: Xaa2 is glycine (Gly) or alanine (Ala)
<220> FEATURE:
<221> NAME/KEY: MISC_FEATURE
<222> LOCATION: (43)..(43)
<223> OTHER INFORMATION: Xaa3 is glutamine (Gln) or histidine (His)

<400> SEQUENCE: 40

Asp Ile Val Met Thr Gln Thr Pro Leu Ser Leu Ser Val Thr Pro Gly
1               5                   10                  15

Gln Pro Ala Ser Ile Ser Cys Arg Ser Ser Lys Ser Leu Leu His Xaa
            20                  25                  30

Asn Xaa Ile Thr Tyr Phe Tyr Trp Tyr Leu Xaa Lys Pro Gly Gln Pro
        35                  40                  45

Pro Gln Leu Leu Ile Tyr Gln Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Leu Thr Phe Gly Gly Gly Thr Lys Val Glu Ile Lys
            100                 105                 110


<210> SEQ ID NO 41
<211> LENGTH: 112
<212> TYPE: PRT
<213> ORGANISM: Artificial Sequence
<220> FEATURE:
<223> OTHER INFORMATION: Synthetic Sequence

<400> SEQUENCE: 41

Asp Ile Val Met Thr Gln Thr Pro Leu Ser Leu Ser Val Thr Pro Gly
1               5                   10                  15

Gln Pro Ala Ser Ile Ser Cys Arg Ser Ser Lys Ser Leu Leu His Ser
            20                  25                  30

Asn Gly Ile Thr Tyr Phe Tyr Trp Tyr Leu Gln Lys Pro Gly Gln Pro
        35                  40                  45

Pro Gln Leu Leu Ile Tyr Gln Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95
```

```
Leu Glu Leu Pro Leu Thr Phe Gly Gly Gly Thr Lys Val Glu Ile Lys
            100                 105                 110


<210> SEQ ID NO 42
<211> LENGTH: 112
<212> TYPE: PRT
<213> ORGANISM: Artificial Sequence
<220> FEATURE:
<223> OTHER INFORMATION: Synthetic Sequence

<400> SEQUENCE: 42

Asp Ile Val Met Thr Gln Thr Pro Leu Ser Leu Ser Val Thr Pro Gly
1               5                   10                  15

Gln Pro Ala Ser Ile Ser Cys Arg Ser Ser Lys Ser Leu Leu His Ser
            20                  25                  30

Asn Ala Ile Thr Tyr Phe Tyr Trp Tyr Leu Gln Lys Pro Gly Gln Pro
        35                  40                  45

Pro Gln Leu Leu Ile Tyr Gln Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Leu Thr Phe Gly Gly Gly Thr Lys Val Glu Ile Lys
            100                 105                 110


<210> SEQ ID NO 43
<211> LENGTH: 112
<212> TYPE: PRT
<213> ORGANISM: Artificial Sequence
<220> FEATURE:
<223> OTHER INFORMATION: Synthetic Sequence

<400> SEQUENCE: 43

Asp Ile Val Met Thr Gln Thr Pro Leu Ser Leu Ser Val Thr Pro Gly
1               5                   10                  15

Gln Pro Ala Ser Ile Ser Cys Arg Ser Ser Lys Ser Leu Leu His Arg
            20                  25                  30

Asn Ala Ile Thr Tyr Phe Tyr Trp Tyr Leu Gln Lys Pro Gly Gln Pro
        35                  40                  45

Pro Gln Leu Leu Ile Tyr Gln Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Leu Thr Phe Gly Gly Gly Thr Lys Val Glu Ile Lys
            100                 105                 110


<210> SEQ ID NO 44
<211> LENGTH: 112
<212> TYPE: PRT
<213> ORGANISM: Artificial Sequence
<220> FEATURE:
<223> OTHER INFORMATION: Synthetic Sequence

<400> SEQUENCE: 44

Asp Ile Val Met Thr Gln Thr Pro Leu Ser Leu Ser Val Thr Pro Gly
1               5                   10                  15

Gln Pro Ala Ser Ile Ser Cys Arg Ser Ser Lys Ser Leu Leu His Arg
```

```
            20                  25                  30

Asn Ala Ile Thr Tyr Phe Tyr Trp Tyr Leu His Lys Pro Gly Gln Pro
        35                  40                  45

Pro Gln Leu Leu Ile Tyr Gln Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Leu Thr Phe Gly Gly Gly Thr Lys Val Glu Ile Lys
            100                 105                 110


<210> SEQ ID NO 45
<211> LENGTH: 107
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (64)..(64)
<223> OTHER INFORMATION: Xaa1 is serine (Ser) or proline (Pro)
<220> FEATURE:
<221> NAME/KEY: MISC_FEATURE
<222> LOCATION: (71)..(71)
<223> OTHER INFORMATION: Xaa2 is phenylalanine (Phe) or tyrosine (Tyr)

<400> SEQUENCE: 45

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Xaa
    50                  55                  60

Ser Gly Ser Gly Thr Asp Xaa Thr Phe Thr Ile Ser Ser Leu Gln Pro
65                  70                  75                  80

Glu Asp Ile Ala Thr Tyr Tyr Cys Gln Gln Gly His Thr Leu Pro Trp
                85                  90                  95

Thr Phe Gly Gly Gly Thr Lys Val Glu Ile Lys
            100                 105


<210> SEQ ID NO 46
<211> LENGTH: 107
<212> TYPE: PRT
<213> ORGANISM: Artificial Sequence
<220> FEATURE:
<223> OTHER INFORMATION: Synthetic Sequence

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro
```

```
65                  70                  75                  80

Glu Asp Ile Ala Thr Tyr Tyr Cys Gln Gln Gly His Thr Leu Pro Trp
                85                  90                  95

Thr Phe Gly Gly Gly Thr Lys Val Glu Ile Lys
            100                 105


<210> SEQ ID NO 47
<211> LENGTH: 107
<212> TYPE: PRT
<213> ORGANISM: Artificial Sequence
<220> FEATURE:
<223> OTHER INFORMATION: Synthetic Sequence

<400> SEQUENCE: 47

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Pro
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln Gln Gly His Thr Leu Pro Trp
                85                  90                  95

Thr Phe Gly Gly Gly Thr Lys Val Glu Ile Lys
            100                 105


<210> SEQ ID NO 48
<211> LENGTH: 112
<212> TYPE: PRT
<213> ORGANISM: Artificial Sequence
<220> FEATURE:
<223> OTHER INFORMATION: Synthetic Sequence

<400> SEQUENCE: 48

Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Ser Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Ser Gly Thr Lys Leu Glu Ile Lys
            100                 105                 110


<210> SEQ ID NO 49
<211> LENGTH: 112
<212> TYPE: PRT
<213> ORGANISM: Artificial Sequence
<220> FEATURE:
<223> OTHER INFORMATION: Synthetic Sequence

<400> SEQUENCE: 49
```

```
Asp Ile Val Met Thr Gln Ala Ala Phe Ser Asn Pro Val Thr Leu Gly
1               5                   10                  15

Thr Ser Ala Ser Ile Ser Cys Arg Ser Ser Lys Ser Leu Leu His Ser
            20                  25                  30

Asn Gly Ile Thr Tyr Phe Tyr Trp Tyr Leu Gln Arg Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Val Gly Ile Tyr Tyr Cys Ala Gln Asn
                85                  90                  95

Leu Glu Leu Pro Leu Thr Phe Gly Ala Gly Thr Lys Leu Glu Leu Lys
            100                 105                 110


<210> SEQ ID NO 50
<211> LENGTH: 107
<212> TYPE: PRT
<213> ORGANISM: Artificial Sequence
<220> FEATURE:
<223> OTHER INFORMATION: Synthetic Sequence

<400> SEQUENCE: 50

Asp Ile Gln Met Thr Gln Thr Thr Ser Ser Leu Ser Ala Ser Leu Gly
1               5                   10                  15

Asp Arg Val Thr Ile Asn Cys Arg Ala Ser Gln Asp Ile Asn Asn Tyr
            20                  25                  30

Leu Asn Trp Tyr Gln Gln Lys Pro Asp Gly Thr Ile Arg Leu Leu Ile
        35                  40                  45

Tyr Tyr Thr Ser Arg Leu His Ser Gly Val Pro Ser Arg Phe Ser Pro
    50                  55                  60

Asn Gly Ser Gly Thr Asp Tyr Ser Leu Thr Ile Asn Asn Leu Glu Gln
65                  70                  75                  80

Glu Asp Ile Ala Thr Tyr Phe Cys Gln Gln Gly His Thr Leu Pro Trp
                85                  90                  95

Thr Phe Gly Gly Gly Thr Lys Leu Glu Ile Lys
            100                 105


<210> SEQ ID NO 51
<211> LENGTH: 117
<212> TYPE: PRT
<213> ORGANISM: Artificial Sequence
<220> FEATURE:
<223> OTHER INFORMATION: Synthetic Sequence

<400> SEQUENCE: 51

Asp Val Gln Phe Gln Glu Ser Gly Pro Gly Leu Val Lys Pro Ser Gln
1               5                   10                  15

Thr Leu Ser Leu Thr Cys Thr Val Thr Gly Tyr Ser Ile Thr Ser Asp
            20                  25                  30

Phe Ala Trp Asn Trp Ile Arg Gln Pro Pro Gly Lys Gly Leu Glu Trp
        35                  40                  45

Ile Gly Tyr Ile Ser Tyr Ser Gly Asp Thr Asn Tyr Asn Pro Ser Leu
    50                  55                  60

Lys Ser Arg Val Thr Ile Thr Arg Asp Thr Ser Lys Asn Gln Phe Ser
65                  70                  75                  80

Leu Lys Leu Ser Ser Val Thr Ala Ala Asp Thr Ala Val Tyr Phe Cys
```

```
                85                  90                  95

Ala Ile Arg Gly Pro Tyr Ser Phe Thr Tyr Trp Gly Gln Gly Thr Leu
            100                 105                 110

Val Thr Val Ser Ser
        115


<210> SEQ ID NO 52
<211> LENGTH: 118
<212> TYPE: PRT
<213> ORGANISM: Artificial Sequence
<220> FEATURE:
<223> OTHER INFORMATION: Synthetic Sequence

<400> SEQUENCE: 52

Asp Val Gln Phe Gln Glu Ser Gly Pro Gly Leu Val Lys Pro Ser Gln
1               5                   10                  15

Thr Leu Ser Leu Thr Cys Thr Val Thr Gly Tyr Ser Ile Thr Ala Asp
            20                  25                  30

Phe Ala Trp Asn Trp Ile Arg Gln Pro Pro Gly Lys Gly Leu Glu Trp
        35                  40                  45

Ile Gly Tyr Ile Ser Tyr Ser Gly Asp Thr Asn Tyr Asn Pro Ser Leu
    50                  55                  60

Lys Ser Arg Val Thr Ile Thr Arg Asp Thr Ser Lys Asn Gln Phe Ser
65                  70                  75                  80

Leu Lys Leu Ser Ser Val Thr Ala Ala Asp Thr Ala Val Tyr Phe Cys
                85                  90                  95

Ala Ile Arg Gly Pro Tyr Ser Phe Thr Tyr Trp Gly Gln Gly Thr Leu
            100                 105                 110

Val Thr Val Ser Ser Ala
        115


<210> SEQ ID NO 53
<211> LENGTH: 118
<212> TYPE: PRT
<213> ORGANISM: Artificial Sequence
<220> FEATURE:
<223> OTHER INFORMATION: Synthetic Sequence

<400> SEQUENCE: 53

Asp Leu Gln Phe Gln Glu Ser Gly Pro Gly Leu Val Lys Pro Ser Gln
1               5                   10                  15

Thr Leu Ser Leu Thr Cys Thr Val Thr Gly Tyr Ser Ile Thr Ala Asp
            20                  25                  30

Phe Ala Trp Asn Trp Ile Arg Gln Pro Pro Gly Lys Gly Leu Glu Trp
        35                  40                  45

Ile Gly Tyr Ile Ser Tyr Ser Gly Asp Thr Asn Tyr Asn Pro Ser Leu
    50                  55                  60

Lys Ser Arg Val Thr Ile Thr Arg Asp Thr Ser Lys Asn Gln Phe Ser
65                  70                  75                  80

Leu Lys Leu Ser Ser Val Thr Ala Ala Asp Thr Ala Val Tyr Phe Cys
                85                  90                  95

Ala Ile Arg Gly Pro Tyr Ser Phe Thr Tyr Trp Gly Gln Gly Thr Leu
            100                 105                 110

Val Thr Val Ser Ser Ala
        115


<210> SEQ ID NO 54
<211> LENGTH: 118
```

```
<212> TYPE: PRT
<213> ORGANISM: Artificial Sequence
<220> FEATURE:
<223> OTHER INFORMATION: Synthetic Sequence

<400> SEQUENCE: 54

Asp Leu Gln Phe Gln Glu Ser Gly Pro Gly Leu Val Lys Pro Ser Gln
1               5                   10                  15

Thr Leu Ser Leu Thr Cys Thr Val Ser Arg Tyr Ser Ile Thr Ala Asp
            20                  25                  30

Phe Ala Trp Asn Trp Ile Arg Gln Pro Pro Gly Lys Gly Leu Glu Trp
        35                  40                  45

Ile Gly Tyr Ile Ser Tyr Ser Gly Asp Thr Asn Tyr Asn Pro Ser Leu
    50                  55                  60

Lys Ser Arg Val Thr Ile Thr Arg Asp Thr Ser Lys Asn Gln Phe Ser
65                  70                  75                  80

Leu Lys Leu Ser Ser Val Thr Ala Ala Asp Thr Ala Val Tyr Phe Cys
                85                  90                  95

Ala Ile Arg Gly Pro Tyr Ser Phe Thr Tyr Trp Gly Gln Gly Thr Leu
            100                 105                 110

Val Thr Val Ser Ser Ala
        115


<210> SEQ ID NO 55
<211> LENGTH: 109
<212> TYPE: PRT
<213> ORGANISM: Artificial Sequence
<220> FEATURE:
<223> OTHER INFORMATION: Synthetic Sequence

<400> SEQUENCE: 55

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Asn Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Met Leu His Ser Gly Val Pro Ser Arg Phe Ser Pro
    50                  55                  60

Ser Gly Ser Gly Asn Asp Tyr Thr Phe Thr Ile Ser Ser Leu Gln Pro
65                  70                  75                  80

Glu Asp Ile Ala Thr Tyr Tyr Cys Gln Gln Gly His Thr Leu Pro Trp
                85                  90                  95

Thr Phe Gly Gly Gly Thr Lys Val Glu Ile Lys Arg Thr
            100                 105


<210> SEQ ID NO 56
<211> LENGTH: 116
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (4)..(4)
<223> OTHER INFORMATION: Xaa1 is leucine (Leu) or phenylalanine (Phe)
<220> FEATURE:
<221> NAME/KEY: MISC_FEATURE
<222> LOCATION: (5)..(5)
<223> OTHER INFORMATION: Xaa2 is valine (Val), methionine (Met), or
      leucine (Leu)
<220> FEATURE:
```

```
<221> NAME/KEY: MISC_FEATURE
<222> LOCATION: (44)..(44)
<223> OTHER INFORMATION: Xaa3 is arginine (Arg) or glycine (Gly)
<220> FEATURE:
<221> NAME/KEY: MISC_FEATURE
<222> LOCATION: (56)..(56)
<223> OTHER INFORMATION: Xaa4 is glycine (Gly), serine (Ser), or alanine
      (Ala)
<220> FEATURE:
<221> NAME/KEY: MISC_FEATURE
<222> LOCATION: (72)..(72)
<223> OTHER INFORMATION: Xaa5 is arginine (Arg) or alanine (Ala)
<220> FEATURE:
<221> NAME/KEY: MISC_FEATURE
<222> LOCATION: (74)..(74)
<223> OTHER INFORMATION: Xaa6 is threonine (Thr) or lysine (Lys)
<220> FEATURE:
<221> NAME/KEY: MISC_FEATURE
<222> LOCATION: (77)..(77)
<223> OTHER INFORMATION: Xaa7 is serine (Ser) or asparagine (Asn)
<220> FEATURE:
<221> NAME/KEY: MISC_FEATURE
<222> LOCATION: (84)..(84)
<223> OTHER INFORMATION: Xaa8 is serine (Ser) or alanine (Ala)
<220> FEATURE:
<221> NAME/KEY: MISC_FEATURE
<222> LOCATION: (95)..(95)
<223> OTHER INFORMATION: Xaa9 is tyrosine (Tyr) or phenylalanine (Phe)

<400> SEQUENCE: 56

Gln Val Gln Xaa Xaa Gln Ser Gly Ala Glu Val Lys Lys Pro Gly Ala
1               5                   10                  15

Ser Val Lys Val Ser Cys Lys Ala Ser Gly Phe Thr Phe Thr Ser Tyr
            20                  25                  30

Asp Ile Asn Trp Val Arg Gln Ala Pro Gly Gln Xaa Leu Glu Trp Met
        35                  40                  45

Gly Trp Ile Tyr Pro Gly Asp Xaa Ser Thr Lys Tyr Asn Glu Lys Phe
    50                  55                  60

Lys Gly Arg Val Thr Ile Thr Xaa Asp Xaa Ser Ala Xaa Thr Ala Tyr
65                  70                  75                  80

Met Glu Leu Xaa Ser Leu Arg Ser Glu Asp Thr Ala Val Tyr Xaa Cys
                85                  90                  95

Thr Arg Ser Phe Tyr Thr Met Asp Tyr Trp Gly Gln Gly Thr Thr Val
            100                 105                 110

Thr Val Ser Ser
        115


<210> SEQ ID NO 57
<211> LENGTH: 118
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: Xaa1 is glutamine (Gln) or aspartic acid (Asp)
<220> FEATURE:
<221> NAME/KEY: MISC_FEATURE
<222> LOCATION: (2)..(2)
<223> OTHER INFORMATION: Xaa2 is valine (Val) or leucine (Leu)
<220> FEATURE:
<221> NAME/KEY: MISC_FEATURE
<222> LOCATION: (4)..(4)
<223> OTHER INFORMATION: Xaa3 is leucine (Leu) or phenylalanine (Phe)
<220> FEATURE:
<221> NAME/KEY: MISC_FEATURE
<222> LOCATION: (25)..(25)
<223> OTHER INFORMATION: Xaa4 is threonine (Thr) or serine (Ser)
<220> FEATURE:
```

```
<221> NAME/KEY: MISC_FEATURE
<222> LOCATION: (26)..(26)
<223> OTHER INFORMATION: Xaa5 is glycine (Gly) or arginine (Arg)
<220> FEATURE:
<221> NAME/KEY: MISC_FEATURE
<222> LOCATION: (31)..(31)
<223> OTHER INFORMATION: Xaa6 serine (Ser) or alanine (Ala)
<220> FEATURE:
<221> NAME/KEY: MISC_FEATURE
<222> LOCATION: (41)..(41)
<223> OTHER INFORMATION: Xaa7 is proline (Pro) or phenylalanine (Phe)
<220> FEATURE:
<221> NAME/KEY: MISC_FEATURE
<222> LOCATION: (44)..(44)
<223> OTHER INFORMATION: Xaa8 is lysine (Lys) or asparagine (Asn)
<220> FEATURE:
<221> NAME/KEY: MISC_FEATURE
<222> LOCATION: (45)..(45)
<223> OTHER INFORMATION: Xaa9 is glycine (Gly) or lysine (Lys)
<220> FEATURE:
<221> NAME/KEY: MISC_FEATURE
<222> LOCATION: (71)..(71)
<223> OTHER INFORMATION: Xaa10 is serine (Ser) or threonine (Thr)
<220> FEATURE:
<221> NAME/KEY: MISC_FEATURE
<222> LOCATION: (72)..(72)
<223> OTHER INFORMATION: Xaa11 is valine (Val) or arginine (Arg)
<220> FEATURE:
<221> NAME/KEY: MISC_FEATURE
<222> LOCATION: (93)..(93)
<223> OTHER INFORMATION: Xaa12 is threonine (Thr) or valine (Val)
<220> FEATURE:
<221> NAME/KEY: MISC_FEATURE
<222> LOCATION: (95)..(95)
<223> OTHER INFORMATION: Xaa13 is tyrosine (Tyr) or phenylalanine (Phe)
<220> FEATURE:
<221> NAME/KEY: MISC_FEATURE
<222> LOCATION: (118)..(118)
<223> OTHER INFORMATION: Xaa14 is is alanine (Ala) or absent

<400> SEQUENCE: 57

Xaa Xaa Gln Xaa Gln Glu Ser Gly Pro Gly Leu Val Lys Pro Ser Gln
1               5                   10                  15

Thr Leu Ser Leu Thr Cys Thr Val Xaa Xaa Tyr Ser Ile Thr Xaa Asp
            20                  25                  30

Phe Ala Trp Asn Trp Ile Arg Gln Xaa Pro Gly Xaa Xaa Leu Glu Trp
        35                  40                  45

Ile Gly Tyr Ile Ser Tyr Ser Gly Asp Thr Asn Tyr Asn Pro Ser Leu
    50                  55                  60

Lys Ser Arg Val Thr Ile Xaa Xaa Asp Thr Ser Lys Asn Gln Phe Ser
65                  70                  75                  80

Leu Lys Leu Ser Ser Val Thr Ala Ala Asp Thr Ala Xaa Tyr Xaa Cys
                85                  90                  95

Ala Ile Arg Gly Pro Tyr Ser Phe Thr Tyr Trp Gly Gln Gly Thr Leu
            100                 105                 110

Val Thr Val Ser Ser Xaa
        115


<210> SEQ ID NO 58
<211> LENGTH: 109
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (28)..(28)
<223> OTHER INFORMATION: Xaa1 is aspartic acid (Asp) or tryptophan (Trp)
<220> FEATURE:
<221> NAME/KEY: MISC_FEATURE
```

<222> LOCATION: (53)..(53)
<223> OTHER INFORMATION: Xaa2 is arginine (Arg) or methionine (Met)
<220> FEATURE:
<221> NAME/KEY: MISC_FEATURE
<222> LOCATION: (64)..(64)
<223> OTHER INFORMATION: Xaa3 is glycine (Gly), serine (Ser) or proline (Pro)
<220> FEATURE:
<221> NAME/KEY: MISC_FEATURE
<222> LOCATION: (69)..(69)
<223> OTHER INFORMATION: Xaa4 is threonine (Thr) or asparagine (Asn)
<220> FEATURE:
<221> NAME/KEY: MISC_FEATURE
<222> LOCATION: (71)..(71)
<223> OTHER INFORMATION: Xaa5 is phenylalanine (Phe) or tyrosine (Tyr)
<220> FEATURE:
<221> NAME/KEY: MISC_FEATURE
<222> LOCATION: (108)..(108)
<223> OTHER INFORMATION: Xaa6 is arginine (Arg) or absent
<220> FEATURE:
<221> NAME/KEY: MISC_FEATURE
<222> LOCATION: (109)..(109)
<223> OTHER INFORMATION: Xaa7 is threonine (Thr) or absent

<400> SEQUENCE: 58

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Xaa Ile Asn Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Xaa Leu His Ser Gly Val Pro Ser Arg Phe Ser Xaa
    50                  55                  60

Ser Gly Ser Gly Xaa Asp Xaa Thr Phe Thr Ile Ser Ser Leu Gln Pro
65                  70                  75                  80

Glu Asp Ile Ala Thr Tyr Tyr Cys Gln Gln Gly His Thr Leu Pro Trp
                85                  90                  95

Thr Phe Gly Gly Gly Thr Lys Val Glu Ile Lys Xaa Xaa
            100                 105
```

<210> SEQ ID NO 59
<211> LENGTH: 9
<212> TYPE: PRT
<213> ORGANISM: Artificial Sequence
<220> FEATURE:
<223> OTHER INFORMATION: synthetic

<400> SEQUENCE: 59

```
Phe Thr Phe Thr Ser Tyr Asp Ile Asn
1               5
```

<210> SEQ ID NO 60
<211> LENGTH: 17
<212> TYPE: PRT
<213> ORGANISM: Artificial Sequence
<220> FEATURE:
<223> OTHER INFORMATION: synthetic

<400> SEQUENCE: 60

```
Trp Ile Tyr Pro Gly Asp Gly Ser Thr Lys Tyr Asn Glu Lys Phe Lys
1               5                   10                  15

Gly
```

<210> SEQ ID NO 61
<211> LENGTH: 17
<212> TYPE: PRT

<213> ORGANISM: Artificial Sequence
<220> FEATURE:
<223> OTHER INFORMATION: synthetic

<400> SEQUENCE: 61

Trp Ile Tyr Pro Gly Asp Ser Ser Thr Lys Tyr Asn Glu Lys Phe Lys
1               5                   10                  15

Gly

<210> SEQ ID NO 62
<211> LENGTH: 17
<212> TYPE: PRT
<213> ORGANISM: Artificial Sequence
<220> FEATURE:
<223> OTHER INFORMATION: synthetic

<400> SEQUENCE: 62

Trp Ile Tyr Pro Gly Asp Ala Ser Thr Lys Tyr Asn Glu Lys Phe Lys
1               5                   10                  15

Gly

<210> SEQ ID NO 63
<211> LENGTH: 7
<212> TYPE: PRT
<213> ORGANISM: Artificial Sequence
<220> FEATURE:
<223> OTHER INFORMATION: synthetic

<400> SEQUENCE: 63

Ser Phe Tyr Thr Met Asp Tyr
1               5

<210> SEQ ID NO 64
<211> LENGTH: 9
<212> TYPE: PRT
<213> ORGANISM: Artificial Sequence
<220> FEATURE:
<223> OTHER INFORMATION: synthetic

<400> SEQUENCE: 64

Tyr Thr Phe Thr Asn Tyr Trp Met His
1               5

<210> SEQ ID NO 65
<211> LENGTH: 9
<212> TYPE: PRT
<213> ORGANISM: Artificial Sequence
<220> FEATURE:
<223> OTHER INFORMATION: synthetic

<400> SEQUENCE: 65

Tyr Thr Phe Thr Asn Tyr Trp Met Asn
1               5

<210> SEQ ID NO 66
<211> LENGTH: 9
<212> TYPE: PRT
<213> ORGANISM: Artificial Sequence
<220> FEATURE:
<223> OTHER INFORMATION: synthetic

<400> SEQUENCE: 66

Tyr Thr Phe Thr Asn Tyr Trp Met Tyr
1               5

<210> SEQ ID NO 67
<211> LENGTH: 9
<212> TYPE: PRT
<213> ORGANISM: Artificial Sequence
<220> FEATURE:
<223> OTHER INFORMATION: synthetic

<400> SEQUENCE: 67

Tyr Thr Phe Thr Asn Tyr Tyr Met Asn
1               5

<210> SEQ ID NO 68
<211> LENGTH: 17
<212> TYPE: PRT
<213> ORGANISM: Artificial Sequence
<220> FEATURE:
<223> OTHER INFORMATION: synthetic

<400> SEQUENCE: 68

Met Phe Asp Pro Ser Asn Ser Val Thr Arg Leu Asn Gln Lys Phe Lys
1               5                   10                  15

Asp

<210> SEQ ID NO 69
<211> LENGTH: 17
<212> TYPE: PRT
<213> ORGANISM: Artificial Sequence
<220> FEATURE:
<223> OTHER INFORMATION: synthetic

<400> SEQUENCE: 69

Met Phe Glu Pro Ser Asn Ala Val Thr Arg Leu Asn Gln Lys Phe Lys
1               5                   10                  15

Asp

<210> SEQ ID NO 70
<211> LENGTH: 17
<212> TYPE: PRT
<213> ORGANISM: Artificial Sequence
<220> FEATURE:
<223> OTHER INFORMATION: synthetic

<400> SEQUENCE: 70

Met Phe His Pro Ser Asn Ala Val Thr Arg Leu Asn Gln Lys Phe Lys
1               5                   10                  15

Asp

<210> SEQ ID NO 71
<211> LENGTH: 17
<212> TYPE: PRT
<213> ORGANISM: Artificial Sequence
<220> FEATURE:
<223> OTHER INFORMATION: synthetic

<400> SEQUENCE: 71

Met Phe His Pro Thr Gly Asp Val Thr Arg Leu Asn Gln Lys Phe Lys
1               5                   10                  15

Asp

<210> SEQ ID NO 72
<211> LENGTH: 11
<212> TYPE: PRT
<213> ORGANISM: Artificial Sequence
<220> FEATURE:
<223> OTHER INFORMATION: synthetic

<400> SEQUENCE: 72

Thr Thr Ser Met Ile Ile Gly Gly Phe Ala Tyr
1 5 10

<210> SEQ ID NO 73
<211> LENGTH: 10
<212> TYPE: PRT
<213> ORGANISM: Artificial Sequence
<220> FEATURE:
<223> OTHER INFORMATION: synthetic

<400> SEQUENCE: 73

Tyr Ser Ile Thr Ser Asp Phe Ala Trp Asn
1 5 10

<210> SEQ ID NO 74
<211> LENGTH: 10
<212> TYPE: PRT
<213> ORGANISM: Artificial Sequence
<220> FEATURE:
<223> OTHER INFORMATION: synthetic

<400> SEQUENCE: 74

Tyr Ser Ile Thr Ala Asp Phe Ala Trp Asn
1 5 10

<210> SEQ ID NO 75
<211> LENGTH: 16
<212> TYPE: PRT
<213> ORGANISM: Artificial Sequence
<220> FEATURE:
<223> OTHER INFORMATION: synthetic

<400> SEQUENCE: 75

Tyr Ile Ser Tyr Ser Gly Asp Thr Asn Tyr Asn Pro Ser Leu Lys Ser
1 5 10 15

<210> SEQ ID NO 76
<211> LENGTH: 8
<212> TYPE: PRT
<213> ORGANISM: Artificial Sequence
<220> FEATURE:
<223> OTHER INFORMATION: synthetic

<400> SEQUENCE: 76

Arg Gly Pro Tyr Ser Phe Thr Tyr
1 5

<210> SEQ ID NO 77
<211> LENGTH: 16
<212> TYPE: PRT
<213> ORGANISM: Artificial Sequence
<220> FEATURE:
<223> OTHER INFORMATION: synthetic

<400> SEQUENCE: 77

Arg Ser Ser Lys Ser Leu Leu His Ser Asn Gly Asn Thr Tyr Leu Tyr
1 5 10 15

<210> SEQ ID NO 78
<211> LENGTH: 16
<212> TYPE: PRT
<213> ORGANISM: Artificial Sequence
<220> FEATURE:
<223> OTHER INFORMATION: synthetic

<400> SEQUENCE: 78

Arg Ser Ser Lys Ser Leu Leu His Ser Asn Ala Asn Thr Tyr Leu Tyr
1 5 10 15

<210> SEQ ID NO 79
<211> LENGTH: 6
<212> TYPE: PRT
<213> ORGANISM: Artificial Sequence
<220> FEATURE:
<223> OTHER INFORMATION: synthetic

<400> SEQUENCE: 79

Arg Met Ser Asn Leu Ala
1 5

<210> SEQ ID NO 80
<211> LENGTH: 9
<212> TYPE: PRT
<213> ORGANISM: Artificial Sequence
<220> FEATURE:
<223> OTHER INFORMATION: synthetic

<400> SEQUENCE: 80

Met Gln His Leu Glu Tyr Pro Phe Thr
1 5

<210> SEQ ID NO 81
<211> LENGTH: 16
<212> TYPE: PRT
<213> ORGANISM: Artificial Sequence
<220> FEATURE:
<223> OTHER INFORMATION: synthetic

<400> SEQUENCE: 81

Arg Ser Ser Lys Ser Leu Leu His Ser Asn Gly Ile Thr Tyr Phe Tyr
1 5 10 15

<210> SEQ ID NO 82
<211> LENGTH: 16
<212> TYPE: PRT
<213> ORGANISM: Artificial Sequence
<220> FEATURE:
<223> OTHER INFORMATION: synthetic

<400> SEQUENCE: 82

Arg Ser Ser Lys Ser Leu Leu His Ser Asn Ala Ile Thr Tyr Phe Tyr
1 5 10 15

<210> SEQ ID NO 83
<211> LENGTH: 16
<212> TYPE: PRT
<213> ORGANISM: Artificial Sequence
<220> FEATURE:
<223> OTHER INFORMATION: synthetic

<400> SEQUENCE: 83

Arg Ser Ser Lys Ser Leu Leu His Arg Asn Ala Ile Thr Tyr Phe Tyr
1 5 10 15

<210> SEQ ID NO 84
<211> LENGTH: 7
<212> TYPE: PRT
<213> ORGANISM: Artificial Sequence
<220> FEATURE:
<223> OTHER INFORMATION: synthetic

<400> SEQUENCE: 84

Gln Met Ser Asn Leu Ala Ser
1 5

<210> SEQ ID NO 85
<211> LENGTH: 9
<212> TYPE: PRT
<213> ORGANISM: Artificial Sequence
<220> FEATURE:
<223> OTHER INFORMATION: synthetic

<400> SEQUENCE: 85

Ala Gln Asn Leu Glu Leu Pro Leu Thr
1 5

<210> SEQ ID NO 86
<211> LENGTH: 11
<212> TYPE: PRT
<213> ORGANISM: Artificial Sequence
<220> FEATURE:
<223> OTHER INFORMATION: synthetic

<400> SEQUENCE: 86

Arg Ala Ser Gln Asp Ile Asn Asn Tyr Leu Asn
1 5 10

<210> SEQ ID NO 87
<211> LENGTH: 11
<212> TYPE: PRT
<213> ORGANISM: Artificial Sequence
<220> FEATURE:
<223> OTHER INFORMATION: synthetic

<400> SEQUENCE: 87

Arg Ala Ser Gln Trp Ile Asn Asn Tyr Leu Asn
1 5 10

<210> SEQ ID NO 88
<211> LENGTH: 7
<212> TYPE: PRT
<213> ORGANISM: Artificial Sequence
<220> FEATURE:
<223> OTHER INFORMATION: synthetic

<400> SEQUENCE: 88

Tyr Thr Ser Arg Leu His Ser
1 5

<210> SEQ ID NO 89
<211> LENGTH: 7
<212> TYPE: PRT
<213> ORGANISM: Artificial Sequence
<220> FEATURE:
<223> OTHER INFORMATION: synthetic

<400> SEQUENCE: 89

Tyr Thr Ser Met Leu His Ser
1 5

<210> SEQ ID NO 90
<211> LENGTH: 9
<212> TYPE: PRT
<213> ORGANISM: Artificial Sequence
<220> FEATURE:
<223> OTHER INFORMATION: synthetic

```
<400> SEQUENCE: 90

Gln Gln Gly His Thr Leu Pro Trp Thr
1               5
```

METHOD OF TREATING ICHTHYOSIS IN A SUBJECT BY ADMINISTERING AN ANTI-INTERLEUKIN 36 RECEPTOR (IL-36R) BINDING AGENT

CROSS-REFERENCE TO RELATED APPLICATIONS

This patent application claims the benefit of U.S. Provisional Patent Application 63/058,938, filed Jul. 30, 2020, which is incorporated by reference in its entirety herein.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: 76,939 Byte ASCII (Text) file named "754349_ST25.TXT," created on Jul. 26, 2021.

BACKGROUND OF THE INVENTION

Ichthyosis is a family of rare, lifelong genetic disorders comprising at least 20 different subtypes. It has been reported that mutations in over 50 genes cause ichthyosis, which affect a host of cellular functions including DNA repair, lipid biosynthesis, adhesion, and desquamation, as well as other pathways. (Marukian, *F1000Research,* 5(F1000 Faculty Rev):1497 (2016)). However, the ichthyoses all share characteristics of generalized or localized scaling, erythema, and underlying skin inflammation. These characteristics are thought to be a compensatory response to the poor epidermal barrier exhibited in all forms of ichthyosis, which is evidenced by the increase in transepidermal water loss (TEWL). Adults and children afflicted with ichthyosis may experience highly visible and disfiguring skin alterations, pruritus, and functional limitations related to thickened skin, which ultimately lead to a poor quality of life.

There is currently no known cure for ichthyosis. Therapy has been limited to emollients and agents, such as keratolytics and retinoids, that peel the thick scales caused by the disorder. While oral retinoids are considered to be an effective treatment method for removing the scales, they tend to increase a subject's ichthyosis-associated skin inflammation and are fraught with potential side effects. Moreover, oral retinoids are not a pathogenesis-based therapy (i.e, pathway-specific therapy), which generally provide therapeutic, safety, and cost-related advantages.

There remains a significant unmet medical need for an effective treatment for ichthyosis.

BRIEF SUMMARY OF THE INVENTION

In an embodiment, the invention provides a method of treating ichthyosis in a subject by inhibiting interleukin 36 (IL-36) signalling in the subject, thereby treating the ichthyosis.

An additional embodiment provides a method of selecting a subject with ichthyosis for treatment with an inhibitor of the IL-36 pathway, which can optionally be used in conjunction with the method of treating ichthyosis in a subject provided herein. In one aspect, the method comprises comparing the expression of at least one of an IL-36 cytokine, IL-36R, or mRNA encoding same in a skin sample from the subject before and after inhibiting IL-36 signalling in the subject, and selecting the subject for treatment when a decrease in expression of at least one of an IL-36 cytokine, IL-36R, or mRNA encoding same is observed in the skin sample from the subject after inhibiting IL-36 signalling as compared to that of the sample from the subject before inhibiting IL-36 signalling.

In further embodiments, the invention provides an inhibitor of the IL-36 pathway, e.g., an IL-36 receptor (IL-36R) binding agent, and composition comprising same, for use in the inventive methods. These and other aspects of the invention will be apparent to the skilled person reading the detailed description.

BRIEF DESCRIPTION OF THE DRAWINGS

FIG. 2B shows protein expression of IL-36R in skin biopsies of control patients (i.e., patients not afflicted with ichthyosis) using IHC.

DETAILED DESCRIPTION OF THE INVENTION

Figure 1A:
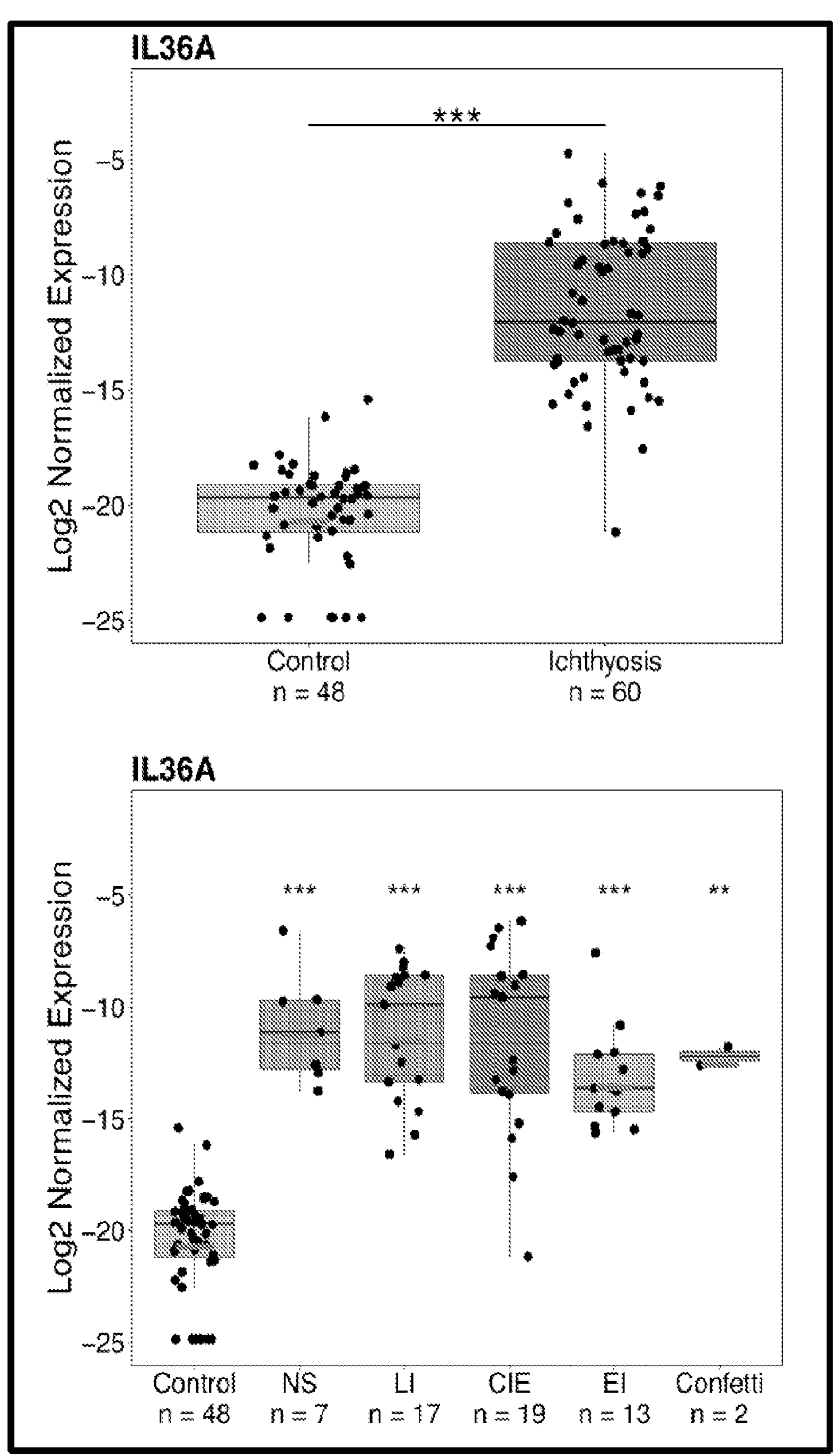
FIG. 1A shows two bar graphs depicting gene expression of IL-36α in skin biopsies patients with ichthyosis (i.e., Netherton syndrome, lamellar ichthyosis, congenital ichthyosiform erythroderma, epidermolytic ichthyosis, and ichthyosis with confetti) as compared to control.

Provided herein is a method of treating ichthyosis in a subject, the method comprising inhibiting IL-36 signaling in the subject, thereby treating the ichthyosis. Inhibiting IL-36 signaling can be accomplished by any suitable method, such as by preventing IL-36 receptor (IL-36R) from binding to one or more (or all) IL-36 cytokines (e.g., IL-36α, IL-36β, and/or IL-36γ).

The IL-36 cytokines IL-36α, IL-36β, and IL-36γ (formerly IL-1F6, IL-1F8, and IL-1F9) are interleukin-1 (IL-1) family members that bind to the IL-36R (formerly IL-1Rrp2 or IL-1RL2), a receptor of the IL-1R family, and use IL-1 receptor accessory protein (IL-1RAcP) as a coreceptor to stimulate intracellular signals similar to those induced by IL-1 (Towne et al., *J. Biol. Chem.,* 279(14): 13677-13688 (2004)). IL-1F5 is an IL-1 family member that has been shown to act as an antagonist of IL-36R, and is now referred to as IL-36Ra (Dinarello et al., *Nat. Immunol.,* 11(11): 973 (2010)).

The ichthyosis described in the method of the embodiment may be any subtype of the ichthyoses, regardless of genotype or phenotype. In some embodiments, the ichthyosis may be associated with Th17 activation in skin, and/or consequent induction of IL-17-related genes or markers synergistically induced by IL-17 and TNF-α. In some embodiments, the ichthyosis is associated with upregulation of IL-36γ compared to a normal subject. In some embodiments, the ichthyosis may be associated with increased CLA+ (skin-homing) T cells of the IL-17+, IL-22+, and IL-9+ subsets compared to a normal subject, or compared to a subject with psoriasis but not ichthyosis. In some embodiments, the ichthyosis is resistant or non-responsive to oral and/or topical retinoids.

In some embodiments, the ichthyoses is a non-syndromic or syndromic ichthyosis. In additional embodiments, the ichthyoses is a common form of ichthyosis (e.g., ichthyosis vulgaris). The ichthyoses also can be an orphan (i.e., rare) form of ichthyosis, including, but not limited to, congenital ichthyosiform erythroderma, lamellar ichthyosis, epidermolytic ichthyosis, Netherton syndrome, and ichthyosis en confetti (ichthyosis with confetti).

The subject can be any subject in need of treatment. In some embodiments, the subject has an IASI score of at least 12, and/or an erythema score of at least 2. The IASI quantifies the severity of a subject's ichthyosis based on the severity of erythema or scaling, and the percentage of BSA affected, and is a composite score ranging from 0 to 48 that that takes into account the degree of erythema and scaling (each scored from 0 to 4 separately) for each of four body regions, with adjustments for the percentage of BSA involved for each body region and for the proportion of the body region to the whole body (see Paller et al., *J Allergy Clin Immunol.,* 139(1):152-165 (2017)). The subject can be a mammal, such as a human or a non-human primate.

As used herein, the terms "treatment," "treating," and the like refer to obtaining a desired pharmacologic and/or physiologic effect. Preferably, the effect is therapeutic, i.e., the treatment reduces the severity of one or more adverse symptoms of ichthyosis, including, but not limited to, scale removal, erythema, inhibition of pruritus, and reduced inflammation. Reduction in adverse symptoms can be determined by any suitable technique, such as a reduction in TEWL or reduction in ichthyosis clinical severity, as defined by the Ichthyosis Area Severity Index (IASI) described in Paller et al., *J Allergy Clin Immunol.,* 139(1):152-165 (2017) and Visual Index for Ichthyosis Severity (VISI) described in Marukian et al., *J Invest Dermatol,* 137:1834-1841 (2017).

To this end, the inventive method comprises administering a "therapeutically effective amount" of an IL-36 pathway inhibitor, such as the IL-36R-binding agent described herein, to a subject.

A "therapeutically effective amount" refers to an amount effective, at dosages and for periods of time necessary, to achieve a desired pharmacologic and/or physiologic effect. The therapeutically effective amount may vary according to factors such as the disease state, age, sex, and weight of the individual, and the ability of the IL-36 pathway inhibitor, e.g., the IL-36R-binding agent, to elicit a desired response in the individual. For example, a therapeutically effective amount of an inhibitor of the IL-36 pathway is an amount that decreases the bioactivity of any one of the IL-36 cytokines and/or IL-36R, such that a therapeutically effective amount of the IL-36R-binding agent described herein is an amount that decreases IL-36R bioactivity in a subject.

In some embodiments, the pharmacologic and/or physiologic effect may be prophylactic, i.e., the effect completely or partially prevents ichthyosis or symptom thereof. In this respect, the inventive method comprises administering a "prophylactically effective amount" of the IL-36 pathway inhibitor. A "prophylactically effective amount" refers to an amount effective, at dosages and for periods of time necessary, to achieve a desired prophylactic result (e.g., prevention of onset of ichthyosis). In some embodiments, the subject can be a subject with a genetic predisposition to ichthyosis (e.g., family history or genetic profile of ichthyosis), with or without any clinical symptoms.

Any suitable dose of an IL-36 inhibitor can be used. In some embodiments, the dose is in the range of 1 pg/kg to 20 mg/kg of animal or human body weight; however, doses below or above this exemplary range are within the scope of the invention. The daily parenteral dose can be about 0.00001 μg/kg to about 20 mg/kg of total body weight (e.g., about 0.001 μg/kg, about 0.1 μg/kg, about 1 μg/kg, about 5 μg/kg, about 10 μg/kg, about 100 μg/kg, about 500 μg/kg, about 1 mg/kg, about 5 mg/kg, about 10 mg/kg, or a range defined by any two of the foregoing values), preferably from about 0.1 μg/kg to about 10 mg/kg of total body weight (e.g., about 0.5 μg/kg, about 1 μg/kg, about 50 μg/kg, about 150 μg/kg, about 300 μg/kg, about 750 μg/kg, about 1.5 mg/kg, about 5 mg/kg, or a range defined by any two of the foregoing values), more preferably from about 1 μg/kg to 5 mg/kg of total body weight (e.g., about 3 μg/kg, about 15 μg/kg, about 75 μg/kg, about 300 μg/kg, about 900 μg/kg, about 2 mg/kg, about 4 mg/kg, or a range defined by any two of the foregoing values), and even more preferably from about 0.5 to 15 mg/kg body weight per day (e.g., about 1 mg/kg, about 2.5 mg/kg, about 3 mg/kg, about 6 mg/kg, about 9 mg/kg, about 11 mg/kg, about 13 mg/kg, or a range defined by any two of the foregoing values).

In some embodiments the dose is about 20 mg or more (e.g., about 30 mg or more, about 50 mg or more, about 75 mg or more, or about 100 mg or more), and about 1000 mg or less (e.g., about 900 mg or less, about 800 mg or less, about 700 mg or less, about 600 mg or less, about 500 mg or less, about 400 mg or less, or about 300 mg or less) every 1-6 weeks (e.g., every week, every two weeks, every three weeks or every four weeks). In some embodiments, the dose is about 150-250 mg (e.g., about 200 mg). In some embodiments, the dose is about In some embodiments, the IL-36 inhibitor is administered in a single loading does of about 1.5×-10× (e.g., about 2×-8×) the amount of following maintenance doses. Thus, for instance, the IL-36 pathway inhibitor can be administered in a loading dose of about 200 mg-750 mg or about 300-500 mg or even about 350-450 mg (e.g., about 200 mg, about 250 mg, about 300 mg, about 350 mg, about 400 mg, about 450 mg, about 500 mg, about 550 mg, about 600 mg, about 650 mg, about 700 mg, or about 750 mg) followed by a maintenance dose of about 50-250 mg or about 100-250 mg, or even about 150-250 mg (e.g., about 50 mg, about 100 mg, about 150 mg, about 200 mg, about 250 mg) every two weeks or every month or two months (e.g., every 2-8 weeks or 2-4 weeks) thereafter as needed to effect or maintain a therapeutic response.

In some embodiments, the IL-36R binding agent provides a long-lasting effect against ichthyosis and allows for relatively infrequent dosing, for instance, on a schedule of not more than once every 14 days, 21 days, or 30 days. In some embodiments, an even longer interval can be used (e.g., not more than once every 45 days, 60 days, 90 days, or 120 days). Thus, for instance, the foregoing doses described herein can be administered once every 14 days, once every 21 days, once every 30 days, once every 45 days, once every 60 days, once every 90 days, or even once every 120 days. When a loading dose is used followed by maintenance doses, the loading dose can be the first dose administered, and the loading doses administered at the following intervals. In an embodiment, the IL-36R binding agent is administered in a loading dose (e.g., 200 mg-750 mg, such as about 350-450 mg or even 400 mg) followed by a maintenance dose (e.g., about 100-250 mg, or even about 150-250 mg, such as about 200 mg) not more than once every two weeks (e.g., not more than once every 21 days or 30 days).

Therapeutic or prophylactic efficacy can be monitored by periodic assessment of treated patients. For repeated administrations over several days or longer, depending on the condition, the treatment can be repeated until a desired suppression of ichthyosis symptoms occurs, or alternatively, the treatment can be continued for the lifetime of the patient. However, other dosage regimens may be useful and are within the scope of the invention. The desired dosage can be delivered by a single bolus administration of the IL-36 pathway inhibitor or composition described herein, by multiple bolus administrations of the IL-36 pathway inhibitor or composition described herein, or by continuous infusion administration of the IL-36 pathway or composition described herein.

The IL-36 pathway inhibitor can be formulated as a composition for administration to a subject (e.g., a mammal, such as a human or non-human primate) by any suitable route of administration, including oral, intravenous, intraperitoneal, subcutaneous, pulmonary, transdermal, intramuscular, intranasal, buccal, sublingual, or suppository administration. The composition preferably is suitable for parenteral administration. The term "parenteral," as used herein, includes intravenous, intramuscular, subcutaneous, rectal, vaginal, and intraperitoneal administration. In some embodiments, the composition is administered to a mammal using peripheral systemic delivery by intravenous, intraperitoneal, or subcutaneous injection.

The composition can comprise the IL-36 pathway inhibitor and a suitable carrier such as are well known in the art. The choice of carrier will be determined, in part, by the particular site to which the composition may be administered and the particular method used to administer the composition. The composition optionally can be sterile. The composition can be frozen or lyophilized for storage and reconstituted in a suitable sterile carrier prior to use. The compositions can be generated in accordance with conventional techniques described in, e.g., Remington: *The Science and Practice of Pharmacy, 21st Edition*, Lippincott Williams & Wilkins, Philadelphia, PA (2001).

Once administered to a mammal (e.g., a human or non-human primate), the biological activity of the IL-36 pathway inhibitor, e.g., the IL-36R-binding agent, can be measured by any suitable method known in the art. For example, the biological activity can be assessed by determining the stability of a particular IL-36R-binding agent. In one embodiment of the invention, the IL-36R-binding agent (e.g., an antibody) has an in vivo half-life between about 30 minutes and 45 days (e.g., about 30 minutes, about 45 minutes, about 1 hour, about 2 hours, about 4 hours, about 6 hours, about 10 hours, about 12 hours, about 1 day, about 5 days, about 10 days, about 15 days, about 25 days, about 35 days, about 40 days, about 45 days, or a range defined by any two of the foregoing values). In another embodiment, the IL-36R-binding agent has an in vivo half-life between about 2 hours and 20 days (e.g., about 5 hours, about 10 hours, about 15 hours, about 20 hours, about 2 days, about 3 days, about 7 days, about 12 days, about 14 days, about 17 days, about 19 days, or a range defined by any two of the foregoing values). In another embodiment, the IL-36R-binding agent has an in vivo half-life between about 10 days and about 40 days (e.g., about 10 days, about 13 days, about 16 days, about 18 days, about 20 days, about 23 days, about 26 days, about 29 days, about 30 days, about 33 days, about 37 days, about 38 days, about 39 days, about 40 days, or a range defined by any two of the foregoing values).

The stability of the IL-36R-binding agent described herein can be measured in terms of the transition mid-point value ($T_m$), which is the temperature where 50% of the amino acid sequence is in its native confirmation, and the other 50% is denatured. In general, the higher the $T_m$, the more stable the protein. In one embodiment of the invention, the IL-36R-binding agent comprises a transition mid-point value ($T_m$) in vitro of about 60-100° C. For example, the IL-36R-binding agent can comprise a $T_m$ in vitro of about 65-80° C. (e.g., 66° C., 68° C., 70° C., 71° C., 75° C., or 79° C.), about 80-90° C. (e.g., about 81° C., 85° C., or 89° C.), or about 90-100° C. (e.g., about 91° C., about 95° C., or about 99° C.).

The stability of the IL-36R-binding agent can be measured using any other suitable assay known in the art, such as, for example, measuring serum half-life, differential scanning calorimetry (DSC), thermal shift assays, and pulse-chase assays. Other methods of measuring protein stability in vivo and in vitro that can be used in the context of the invention are described in, for example, *Protein Stability and Folding*, B. A. Shirley (ed.), Human Press, Totowa, New Jersey (1995); *Protein Structure, Stability, and Interactions (Methods in Molecular Biology)*, Shiver J. W. (ed.), Humana Press, New York, NY (2010); and Ignatova, *Microb. Cell Fact.*, 4: 23 (2005).

The biological activity of a particular IL-36 pathway inhibitor, e.g., an IL-36R-binding agent, also can be assessed by determining its binding affinity to, e.g., IL-36R or an epitope thereof. The term "affinity" refers to the equilibrium constant for the reversible binding of two agents and is expressed as the dissociation constant ($K_D$). Affinity of a binding agent to a ligand, such as affinity of an antibody for an epitope, can be, for example, from about 1 picomolar (pM) to about 100 micromolar (μM) (e.g., from about 1 picomolar (pM) to about 1 nanomolar (nM), from about 1 nM to about 1 micromolar (μM), or from about 1 μM to about 100 μM). In one embodiment, the IL-36R-binding agent can bind to an IL-36R protein with a $K_D$ less than or equal to 1 nanomolar (e.g., 0.9 nM, 0.8 nM, 0.7 nM, 0.6 nM, 0.5 nM, 0.4 nM, 0.3 nM, 0.2 nM, 0.1 nM, 0.05 nM, 0.025 nM, 0.01 nM, 0.001 nM, or a range defined by any two of the foregoing values). In another embodiment, the IL-36R-binding agent can bind to IL-36R with a $K_D$ less than or equal to 200 pM (e.g., 190 pM, 175 pM, 150 pM, 125 pM, 110 pM, 100 pM, 90 pM, 80 pM, 75 pM, 60 pM, 50 pM, 40 pM, 30 pM, 25 pM, 20 pM, 15 pM, 10 pM, 5 pM, 1 pM, or a range defined by any two of the foregoing values). Immunoglobulin affinity for an antigen or epitope of interest can be measured using any art-recognized assay. Such methods include, for example, fluorescence activated cell sorting (FACS), separable beads (e.g., magnetic beads), surface plasmon resonance (SPR), solution phase competition (KINEXA™), antigen panning, competitive binding assays, and/or ELISA (see, e.g., Janeway et al. (eds.), *Immunobiology*, 5th ed., Garland Publishing, New York, NY, 2001).

The IL-36R-binding agent of the invention may be administered alone or in combination with other drugs. For example, the IL-36R-binding agent can be administered in combination with other agents for the treatment or prevention of the diseases disclosed herein, such as an anti-inflammatory agent including, for example, corticosteroids (e.g., prednisone and fluticasone), non-steroidal anti-inflammatory drugs (NSAIDs) (e.g., aspirin, ibuprofen, and naproxen), biologics (e.g., infliximab (REMICADE™), adalimumab (HUMIRA™), or etanercept (ENBREL™)), methotrexate (MTX), an oral retinoid (e.g. acitretin (SO-RIATANE™)), topical steroids, anti-infectives and/or antibiotics, or other agents useful for alleviating the severity of ichthyosis symptoms.

Patient Population and Methods for Selecting Suitable Patients for Treatment

The patient/subject can be any patient/subject with ichthyosis. In one embodiment, the subject of the present method has increased skin expression of at least one of an IL-36 cytokine, IL-36R, or mRNA encoding same as compared to a normal, non-diseased subject. In a further embodiment, the IL-36 cytokine is IL-36α, IL-36β, or IL-36γ. In particular embodiments, the IL-36 cytokine is IL-36γ. In some embodiments, the increased skin expression of the IL-36 cytokine (e.g., IL-36γ) is at least about 25% higher (e.g., at least about 30% higher, or at least about 50% higher) than the normal baseline expression of a healthy subject.

In a further embodiment, the invention provides a method for selecting a subject (e.g., a mammal) with ichthyosis for treatment with an inhibitor of the IL-36 pathway comprising comparing the expression of at least one of an IL-36 cytokine, IL-36R, or mRNA encoding same in a skin sample from the subject before and after the inhibitor of the IL-36 pathway has been administered to the subject; and selecting the subject for treatment when a decrease in expression of at least one of an IL-36 cytokine, IL-36R, or mRNA encoding same is observed in the skin sample from the subject after administration of the inhibitor of the IL-36 pathway as compared to that of the sample from the subject before administration of the inhibitor of the IL-36 pathway. In one embodiment, the IL-36 cytokine is IL-36α, IL-36β, or IL-36γ. In a further embodiment, the IL-36 pathway inhibitor is the IL-36R-binding agent described herein.

The IL-36 cytokine and IL-36R protein levels of subject can be measured using any suitable method known in the art. Such methods include, for example, radioimmunoassay (RIA), and FACS. Normal or standard expression values of the IL-36 cytokine or IL-36R can be established using any suitable technique, e.g., by combining a sample comprising, or suspected of comprising, IL-36 cytokine or IL-36R with an IL-36 cytokine-specific or IL-36R-specific antibody under conditions suitable to form an antigen-antibody complex. The antibody may be directly or indirectly labeled with a detectable substance to facilitate detection of the bound or unbound antibody. Suitable detectable substances include various enzymes, prosthetic groups, fluorescent materials, luminescent materials, and radioactive materials (see, e.g., Zola, *Monoclonal Antibodies: A Manual of Techniques*, CRC Press, Inc. (1987)).

In addition, or instead, the method for selecting a subject can comprise determining the at the subject has increased Th17 activation in skin as compared to a normal subject, or increased CLA+ (skin-homing) T cells of the IL-17+, IL-22+, and IL-9+ subsets compared to a normal subject, or compared to a subject with psoriasis but not ichthyosis. Suitable techniques for measuring Th17 activation or increased CLA+ T-cells are known in the art.

In addition, or instead, the method of selecting a subject for treatment can include determining that the subject has an IASI score of at least 12, and/or an erythema score of at least 2. The IASI quantifies the severity of a subject's ichthyosis based on the severity of erythema or scaling, and the percentage of BSA affected, and is a composite score ranging from 0 to 48 that that takes into account the degree of erythema and scaling (each scored from 0 to 4 separately) for each of four body regions, with adjustments for the percentage of BSA involved for each body region and for the proportion of the body region to the whole body (see Paller et al., *J Allergy Clin Immunol.,* 139(1):152-165 (2017)). Methods for making such determinations are known in the art.

The method of selecting a subject for treatment can be used in conjunction with the method of treating ichthyosis as described herein.

The IL-36 Pathway Inhibitor

Any of the foregoing methods are not limited to the use of any particular IL-36 pathway inhibitor, provided the inhibitor has an effect that is sufficiently rapid and persistent to allow for a therapeutic effect within the dosing parameters described herein. For example, the IL-36 pathway inhibitor may be any inhibitor that inhibits or neutralizes the IL-36 pathway, e.g., at the level of the cytokines (i.e., inhibits or neutralizes the biological activity of IL-36α, IL-36β, or IL-36γ), the receptor (i.e., inhibits or neutralizes the biological activity of IL-36R), or inhibits or neutralizes the subsequent intracellular signaling induced by the IL-36 cytokines or IL-36R. The method can include, for instance, administering to a subject in need thereof an agent that specifically binds to IL-36R; an agent that specifically binds to an IL-36 cytocine (e.g., IL-36α, IL-36β, or IL-36γ); or a combination thereof. Examples of IL-36 pathway inhibitors including antibodies or antigen binding fragments thereof that bind to an IL-36 cytocine (e.g., IL-36α, IL-36β, or IL-36γ) or IL-36R, several of which are known in the art including sepsolimab (Boehringer Ingleheim), ANB-019 (AnaptysBio, Inc.), and any of the compounds and compositions disclosed in WO2016168542A1; WO 2020018503 A2; WO2019177883A2; WO2018183173A1; U.S. Ser. No. 10/550,189B2; U.S. Pat. No. 9,023,995B2; or WO2013074569A1, all of which are hereby incorporated by reference.

In an embodiment, the IL-36 pathway inhibitor is an IL-36R binding agent, such as an antibody or antigent-binding antibody fragment. An antibody or antigen-binding antibody fragment comprises, consists of, or consists essentially of an immunoglobulin heavy chain polypeptide and an immunoglobulin light chain polypeptide, or at least the variable regions (e.g., antigen-binding fragments) thereof.

A whole immunoglobulin typically consists of four polypeptides: two identical copies of a heavy (H) chain polypeptide and two identical copies of a light (L) chain polypeptide. Each of the heavy chains contains one N-terminal variable ($V_H$) region and three C-terminal constant ($C_H1$, $C_H2$, and $C_H3$) regions, and each light chain contains one N-terminal variable ($V_L$) region and one C-terminal constant (CO region. The light chains of antibodies can be assigned to one of two distinct types, either kappa (κ) or lambda (λ), based upon the amino acid sequences of their constant domains. In a typical immunoglobulin, each light chain is linked to a heavy chain by disulfide bonds, and the two heavy chains are linked to each other by disulfide bonds. The light chain variable region is aligned with the variable region of the heavy chain, and the light chain constant region is aligned with the first constant region of the heavy chain. The remaining constant regions of the heavy chains are aligned with each other.

The variable regions of each pair of light and heavy chains form the antigen binding site of an antibody. The $V_H$ and $V_L$ regions have the same general structure, with each region comprising four framework (FW or FR) regions. The term "framework region," as used herein, refers to the relatively conserved amino acid sequences within the variable region which are located between the hypervariable or complementary determining regions (CDRs). There are four framework regions in each variable domain, which are designated FR1, FR2, FR3, and FR4. The framework regions form the β sheets that provide the structural framework of the variable region (see, e.g., C. A. Janeway et al. (eds.), *Immunobiology, 5th Ed*., Garland Publishing, New York, NY (2001)).

The framework regions are connected by three complementarity determining regions (CDRs). As discussed above, the three CDRs, known as CDR1, CDR2, and CDR3, form the "hypervariable region" of an antibody, which is responsible for antigen binding. The CDR regions also can be referred to using an "H" or "L" in the nomenclature to denote the heavy or light chain, respectively, i.e., CDRH1, CDRH2, CDRH3, CDRL1, CDRL2, or CDRL3. The CDRs of a given Ig sequence can be determined by any of several conventional numbering schemes, such as Kabat, Chothia, Martin (Enhanced Chothia), IGMT, or AHo (see, e.g., Kabat, et al., *Sequences of Proteins of Immunological Interest*, U.S. Department of Health and Human Services, NIH (1991); Chothia, et al., *Canonical Structures for the Hypervariable Regions of Immunoglobulins*, J. Mol. Biol., 196:901-917 (1987); Al-Lazikani et al., *Standard Conformations for the Canonical Structures of Immunoglobulins*, J. Mol. Biol., 273:927-948 (1997); Abhinandan et al., *Analysis and Improvements to Kabat and Structurally Correct Numbering of Antibody Variable Domains*, Mol. Immunol., 45: 3832-3839 (2008); Lefranc et al., *The IMGT unique numbering for immunoglobulins, T cell Receptors and Ig-like domains*, The Immunologist, 7: 132-136 (1999); Lefranc et al., *IMGT unique numbering for immunoglobulin and T cell receptor variable domains and I superfamily V-like domains*, Dev. Comp. Immunol., 27: 55-77 (2003); and Honegger et al., *Yet another numbering scheme for immunoglobulin variable domains: an automatic modeling and analysis tool*, J. Mol. Biol. 309: 657-670 (2001).

In one embodiment, the immunoglobulin heavy chain variable region comprises, consists of, or consists essentially of the amino acid sequence of Gln Val Gln Xaa1 Xaa2 Gln Ser Gly Ala Glu Val Lys Lys Pro Gly Ala Ser Val Lys Val Ser Cys Lys Ala Ser Gly Phe Thr Phe Thr Ser Tyr Asp Ile Asn Trp Val Arg Gln Ala Pro Gly Gln Xaa3 Leu Glu Trp Met Gly Trp Ile Tyr Pro Gly Asp Xaa4 Ser Thr Lys Tyr Asn Glu Lys Phe Lys Gly Arg Val Thr Ile Thr Xaa5 Asp Xaa6 Ser Ala Xaa7 Thr Ala Tyr Met Glu Leu Xaa8 Ser Leu Arg Ser Glu Asp Thr Ala Val Tyr Xaa9 Cys Thr Arg Ser Phe Tyr Thr Met Asp Tyr Trp Gly Gln Gly Thr Thr Val Thr Val Ser Ser (SEQ ID NO: 56), or at least the CDRs thereof, wherein (a) Xaa1 is leucine (Leu) or phenylalanine (Phe), (b) Xaa2 is valine (Val), methionine (Met), or leucine (Leu), (c) Xaa3 is arginine (Arg) or glycine (Gly), (d) Xaa4 is glycine (Gly), serine (Ser), or alanine (Ala), (e) Xaa5 is arginine (Arg) or alanine (Ala), (f) Xaa6 is threonine (Thr) or lysine (Lys), (g) Xaa7 is serine (Ser) or asparagine (Asn), (h) Xaa8 is serine (Ser) or alanine (Ala), and (i) Xaa9 is tyrosine (Tyr) or phenylalanine (Phe). In some embodiments, the immunoglobulin heavy chain polypeptide comprises, consists of, or consists essentially of the amino acid sequence Gln Val Gln Xaa1 Xaa2 Gln Ser Gly Ala Glu Val Lys Lys Pro Gly Ala Ser Val Lys Val Ser Cys Lys Ala Ser Gly Phe Thr Phe Thr Ser Tyr Asp Ile Asn Trp Val Arg Gln Ala Pro Gly Gln Xaa3 Leu Glu Trp Met Gly Trp Ile Tyr Pro Gly Asp Xaa4 Ser Thr Lys Tyr Asn Glu Lys Phe Lys Gly Arg Val Thr Ile Thr Xaa5 Asp Xaa6 Ser Ala Ser Thr Ala Tyr Met Glu Leu Xaa7 Ser Leu Arg Ser Glu Asp Thr Ala Val Tyr Xaa8 Cys Thr Arg Ser Phe Tyr Thr Met Asp Tyr Trp Gly Gln Gly Thr Thr Val Thr Val Ser Ser (SEQ ID NO: 1), or at least the CDRs thereof, wherein (a) Xaa1 is leucine (Leu) or phenylalanine (Phe), (b) Xaa2 is valine (Val), methionine (Met), or leucine (Leu), (c) Xaa3 is arginine (Arg) or glycine (Gly), (d) Xaa4 is glycine (Gly), serine (Ser), or alanine (Ala), (e) Xaa5 is arginine (Arg) or alanine (Ala), (f) Xaa6 is threonine (Thr) or lysine (Lys), (g) Xaa7 is serine (Ser) or alanine (Ala), and (h) Xaa8 is tyrosine (Tyr) or phenylalanine (Phe).

The heavy chain polypeptide can comprise, consist of, or consist essentially of the amino acid sequence of SEQ ID NO: 56 or SEQ ID NO: 1, or at least the CDRs thereof, with any one of the aforementioned amino acid substitutions in any suitable combination. In one embodiment, the immunoglobulin heavy chain polypeptide comprises, consists of, or consists essentially of an amino acid sequence of any one of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, or SEQ ID NO: 14, or at least the CDRs thereof.

In some embodiments, the IL-36R binding agent comprises: a CDR1 of the heavy chain variable region (HCDR1) comprising, consisting of, or consisting essentially of the amino acid sequence Phe Thr Phe Thr Ser Tyr Asp Ile Asn (SEQ ID NO: 59); a CDR2 of the heavy chain variable region (HCDR2) comprising, consisting of, or consisting essentially of the amino acid sequence of (a) Trp Ile Tyr Pro Gly Asp Gly Ser Thr Lys Tyr Asn Glu Lys Phe Lys Gly (SEQ ID NO: 60); (b) Trp Ile Tyr Pro Gly Asp Ser Ser Thr Lys Tyr Asn Glu Lys Phe Lys Gly (SEQ ID NO: 61); or (c) Trp Ile Tyr Pro Gly Asp Ala Ser Thr Lys Tyr Asn Glu Lys Phe Lys Gly (SEQ ID NO: 62); and/or a CDR3 of the heavy chain variable region (HCDR3) comprising, consisting of, or consisting essentially of the amino acid sequence Ser Phe Tyr Thr Met Asp Tyr (SEQ ID NO: 63).

In another embodiment, the immunoglobulin heavy chain variable region comprises, consists of, or consists essentially of the amino acid sequence Gln Val Gln Leu Val Gln Ser Gly Ala Glu Val Lys Lys Pro Gly Ala Ser Val Lys Val Ser Cys Lys Ala Ser Gly Tyr Thr Phe Thr Asn Tyr Xaa1 Met Xaa2 Trp Val Arg Gln Ala Pro Xaa3 Gln Gly Leu Glu Trp Met Gly Met Phe Xaa4 Pro Xaa5 Xaa6 Xaa7 Val Thr Arg Leu Asn Gln Lys Phe Lys Asp Arg Val Thr Met Thr Arg Asp Thr Ser Thr Ser Thr Val Tyr Met Glu Leu Ser Ser Leu Arg Ser Glu Asp Thr Ala Val Tyr Tyr Cys Ala Arg Thr Thr Ser Met Ile Ile Gly Gly Phe Ala Tyr Trp Gly Gln Gly Thr Leu Val Thr Val Ser Ser (SEQ ID NO: 15), or at least the CDRs thereof, wherein (a) Xaa1 is tryptophan (Trp) or tyrosine (Tyr), (b) Xaa2 is histidine (His), asparagine (Asn), or tyrosine (Tyr), (c) Xaa3 is glycine (Gly) or arginine (Arg), (d) Xaa4 is aspartic acid (Asp), glutamic acid (Glu), or histidine (His), (e) Xaa5 is serine (Ser), threonine (Thr), or tyrosine (Tyr), (f) Xaa6 is asparagine (Asn) or glycine (Gly), and (g) Xaa7 is serine (Ser), alanine (Ala), or aspartic acid (Asp).

The heavy chain variable region can comprise, consist of, or consist essentially of the amino acid sequence of SEQ ID NO: 15, or at least the CDRs thereof, with one of the aforementioned amino acid substitutions in any suitable combination. In one embodiment, the immunoglobulin heavy chain polypeptide comprises, consists of, or consists essentially of an amino acid sequence of any one of SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, or SEQ ID NO: 24, or at least the CDRs thereof.

In one embodiment, the IL-36 pathway inhibitor comprises a heavy chain variable region comprising: an HCDR1 comprising, consisting of, or consisting essentially of the amino acid sequence selected from the group consisting of (a) Tyr Thr Phe Thr Asn Tyr Trp Met His (SEQ ID NO: 64); (b) Tyr Thr Phe Thr Asn Tyr Trp Met Asn (SEQ ID NO: 65); (c) Tyr Thr Phe Thr Asn Tyr Trp Met Tyr (SEQ ID NO: 66); and (d) Tyr Thr Phe Thr Asn Tyr Tyr Met Asn (SEQ ID NO: 67); an HCDR2 comprising, consisting of, or consisting essentially of the amino acid sequence selected from the group consisting of (a) Met Phe Asp Pro Ser Asn Ser Val Thr Arg Leu Asn Gln Lys Phe Lys Asp (SEQ ID NO: 68); (b) Met Phe Glu Pro Ser Asn Ala Val Thr Arg Leu Asn Gln Lys Phe Lys Asp (SEQ ID NO: 69); (c) Met Phe His Pro Ser Asn Ala Val Thr Arg Leu Asn Gln Lys Phe Lys Asp (SEQ ID NO: 70); and (d) Met Phe His Pro Thr Gly Asp Val Thr Arg Leu Asn Gln Lys Phe Lys Asp (SEQ ID NO: 71); and/or an HCDR3 comprising, consisting of, or consisting essentially of the amino acid sequence Thr Thr Ser Met Ile Ile Gly Gly Phe Ala Tyr (SEQ ID NO: 72).

In a further embodiment, the immunoglobulin heavy chain variable region comprises, consists of, or consists essentially of the amino acid sequence of Xaa1 Xaa2 Gln Xaa3 Gln Glu Ser Gly Pro Gly Leu Val Lys Pro Ser Gln Thr Leu Ser Leu Thr Cys Thr Val Xaa4 Xaa5 Tyr Ser Ile Thr Xaa6 Asp Phe Ala Trp Asn Trp Ile Arg Gln Xaa7 Pro Gly Xaa8 Xaa9 Leu Glu Trp Ile Gly Tyr Ile Ser Tyr Ser Gly Asp Thr Asn Tyr Asn Pro Ser Leu Lys Ser Arg Val Thr Ile Xaa10 Xaa11 Asp Thr Ser Lys Asn Gln Phe Ser Leu Lys Leu Ser Ser Val Thr Ala Ala Asp Thr Ala Xaa12 Tyr Xaa13 Cys Ala Ile Arg Gly Pro Tyr Ser Phe Thr Tyr Trp Gly Gln Gly Thr Leu Val Thr Val Ser Ser Xaa14 (SEQ ID NO: 57), or at least the CDRs thereof, wherein Xaa1 is glutamine (Gln) or aspartic acid (Asp); Xaa2 is valine (Val) or leucine (Leu); Xaa3 is leucine (Leu) or phenylalanine (Phe); Xaa4 is threonine (Thr) or serine (Ser); Xaa5 is glycine (Gly) or arginine (Arg); Xaa6 serine (Ser) or alanine (Ala); Xaa7 is proline (Pro) or phenylalanine (Phe); Xaa8 is lysine (Lys) or asparagine (Asn); Xaa9 is glycine (Gly) or lysine (Lys); Xaa10 is serine (Ser) or threonine (Thr); Xaa11 is valine (Val) or arginine (Arg); Xaa12 is threonine (Thr) or valine (Val); Xaa13 is tyrosine (Tyr) or phenylalanine (Phe); and Xaa14 is alanine (Ala) or absent. In some embodiments, the heavy chain variable region comprises, consists of, or consists essentially of the amino acid sequence Xaa1 Val Gln Xaa2 Gln Glu Ser Gly Pro Gly Leu Val Lys Pro Ser Gln Thr Leu Ser Leu Thr Cys Thr Val Xaa3 Gly Tyr Ser Ile Thr Ser Asp Phe Ala Trp Asn Trp Ile Arg Gln Xaa4 Pro Gly Xaa5 Xaa6 Leu Glu Trp Ile Gly Tyr Ile Ser Tyr Ser Gly Asp Thr Asn Tyr Asn Pro Ser Leu Lys Ser Arg Val Thr Ile Xaa7 Xaa8 Asp Thr Ser Lys Asn Gln Phe Ser Leu Lys Leu Ser Ser Val Thr Ala Ala Asp Thr Ala Val Tyr Xaa9 Cys Ala Ile Arg Gly Pro Tyr Ser Phe Thr Tyr Trp Gly Gln Gly Thr Leu Val Thr Val Ser Ser (SEQ ID NO: 25), or at least the CDRs thereof, wherein (a) Xaa1 is glutamine (Gln) or aspartic acid (Asp), (b) Xaa2 is leucine (Leu) or phenylalanine (Phe), (c) Xaa3 is threonine (Thr) or serine (Ser), (d) Xaa4 is proline (Pro) or phenylalanine (Phe), (e) Xaa5 is lysine (Lys) or asparagine (Asn), (f) Xaa6 is glycine (Gly) or lysine (Lys), (g) Xaa7 is serine (Ser) or threonine (Thr), (h) Xaa8 is valine (Val) or arginine (Arg), and (i) Xaa9 is tyrosine (Tyr) or phenylalanine (Phe).

In some embodiments, the heavy chain variable region can comprise, consist of, or consist essentially of the amino acid sequence of SEQ ID NO: 57 or SEQ ID NO: 25, or at least the CDRs thereof, with one or more of the aforementioned amino acid substitutions in any suitable combination. In one embodiment, the immunoglobulin heavy chain variable region comprises, consists of, or consists essentially of an amino acid sequence of any one of SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 51, SEQ ID NO: 52, SEQ ID NO: 53, or SEQ ID NO: 54, or at least the CDRs thereof.

In additional embodiments, the IL-36 pathway inhibitor may comprise an HCDR1 comprising, consisting of, or consisting essentially of the amino acid sequence selected from the group consisting of (a) Tyr Ser Ile Thr Ser Asp Phe Ala Trp Asn (SEQ ID NO: 73); and (b) Tyr Ser Ile Thr Ala Asp Phe Ala Trp Asn (SEQ ID NO: 74); an HCDR2 comprising, consisting of, or consisting essentially of the amino acid sequence Tyr Ile Ser Tyr Ser Gly Asp Thr Asn Tyr Asn Pro Ser Leu Lys Ser (SEQ ID NO: 75); and/or an HCDR3 comprising, consisting of, or consisting essentially of the amino acid sequence Arg Gly Pro Tyr Ser Phe Thr Tyr (SEQ ID NO: 76).

In another embodiment, the IL-36 pathway inhibitor comprises an immunoglobulin heavy chain polypeptide which comprises, consists of, or consists essentially of the amino acid sequence of SEQ ID NO: 33, SEQ ID NO: 34, or SEQ ID NO: 35, or at least the CDRs thereof.

In some embodiments, the immunoglobulin heavy chain polypeptide comprises an amino acid sequence that is at least 90% identical (e.g., at least 91%, at least 92%, at least 93%, at least 94%, at least 95%, at least 96%, at least 97%, at least 98%, at least 99%, or 100% identical) to any of the foregoing variable region sequences. Nucleic acid or amino acid sequence "identity," as described herein, can be determined by comparing a nucleic acid or amino acid sequence of interest to a reference nucleic acid or amino acid sequence. The percent identity is the number of nucleotides or amino acid residues that are the same (i.e., that are identical) as between the sequence of interest and the reference sequence divided by the length of the longest sequence (i.e., the length of either the sequence of interest or the reference sequence, whichever is longer). A number of mathematical algorithms for obtaining the optimal alignment and calculating identity between two or more sequences are known and incorporated into a number of available software programs. Examples of such programs include CLUSTAL-W, T-Coffee, and ALIGN (for alignment of nucleic acid and amino acid sequences), BLAST programs (e.g., BLAST 2.1, BL2SEQ, and later versions thereof) and FASTA programs (e.g., FASTA3×, FASTM, and SSEARCH) (for sequence alignment and sequence similarity searches). Sequence alignment algorithms also are disclosed in, for example, Altschul et al., *J. Molecular Biol.,* 215(3): 403-410 (1990), Beigert et al., *Proc. Natl. Acad. Sci. USA,* 106(10): 3770-3775 (2009), Durbin et al., eds., *Biological Sequence Analysis: Probabalistic Models of Proteins and Nucleic Acids*, Cambridge University Press, Cambridge, UK (2009), Soding, *Bioinformatics,* 21(7): 951-960 (2005), Altschul et al., *Nucleic Acids Res.,* 25(17): 3389-3402 (1997), and Gusfield, *Algorithms on Strings, Trees and Sequences*, Cambridge University Press, Cambridge UK (1997)).

In addition to a heavy chain variable region as described herein, the IL-36R binding agent comprises an immunoglobulin light chain variable region that comprises, consists of, or consists essentially of the amino acid sequence Asp Ile Val Met Thr Gln Ser Pro Leu Ser Leu Pro Val Thr Pro Gly Glu Pro Ala Ser Ile Ser Cys Arg Ser Ser Lys Ser Leu Leu His Ser Asn Xaa1 Asn Thr Tyr Leu Tyr Trp Xaa2 Leu Gln Lys Pro Gly Gln Ser Pro Gln Leu Leu Ile Xaa3 Arg Met Ser Asn Leu Ala Ser Gly Val Pro Asp Arg Phe Ser Gly Ser Gly Ser Gly Thr Asp Phe Thr Leu Lys Ile Ser Arg Val Glu Ala Glu Asp Val Gly Val Tyr Tyr Cys Met Gln His Leu Glu Tyr Pro Phe Thr Phe Gly Gln Gly Thr Lys Leu Glu Ile Lys (SEQ ID NO: 36), or at least the CDRs thereof, wherein (a) Xaa1 is glycine (Gly) or alanine (Ala), (b) Xaa2 is phenylalanine (Phe) or tyrosine (Tyr), and (c) Xaa3 is tyrosine (Tyr) or serine (Ser).

The light chain variable region can comprise, consist of, or consist essentially of the amino acid sequence of SEQ ID NO: 36, or at least the CDRs thereof, with one or more of the aforementioned amino acid substitutions in any suitable combination. In one embodiment, the isolated immunoglobulin light chain variable region comprises, consists of, or consists essentially of an amino acid sequence of any one of SEQ ID NO: 37, SEQ ID NO: 38, or SEQ ID NO: 39, or at least the CDRs thereof.

In some embodiments, the IL-36R binding agent comprises a CDR1 of the light chain variable region (LCDR1) comprising, consisting of, or consisting essentially of the amino acid sequence selected of (a) Arg Ser Ser Lys Ser Leu Leu His Ser Asn Gly Asn Thr Tyr Leu Tyr (SEQ ID NO: 77); or (b) Arg Ser Ser Lys Ser Leu Leu His Ser Asn Ala Asn Thr Tyr Leu Tyr (SEQ ID NO: 78); a CDR2 of the light chain variable region (LCDR2) comprising, consisting of, or consisting essentially of the amino acid sequence Arg Met Ser Asn Leu Ala Ser (SEQ ID NO: 79); and a CDR3 of the light chain variable region (LCDR3) comprising, consisting of, or consisting essentially of the amino acid sequence Met Gln His Leu Glu Tyr Pro Phe Thr (SEQ ID NO: 80).

In some embodiments, the immunoglobulin light chain variable region comprises, consists of, or consists essentially of the amino acid sequence Asp Ile Val Met Thr Gln Thr Pro Leu Ser Leu Ser Val Thr Pro Gly Gln Pro Ala Ser Ile Ser Cys Arg Ser Ser Lys Ser Leu Leu His Xaa1 Asn Xaa2 Ile Thr Tyr Phe Tyr Trp Tyr Leu Xaa3 Lys Pro Gly Gln Pro Pro Gln Leu Leu Ile Tyr Gln Met Ser Asn Leu Ala Ser Gly Val Pro Asp Arg Phe Ser Gly Ser Gly Ser Gly Thr Asp Phe Thr Leu Lys Ile Ser Arg Val Glu Ala Glu Asp Val Gly Val Tyr Tyr Cys Ala Gln Asn Leu Glu Leu Pro Leu Thr Phe Gly Gly Gly Thr Lys Val Glu Ile Lys (SEQ ID NO: 40), or at least the CDRs thereof, wherein (a) Xaa1 is serine (Ser) or arginine (Arg), (b) Xaa2 is glycine (Gly) or alanine (Ala), and (c) Xaa3 is glutamine (Gln) or histidine (His).

The light chain variable region can comprise, consist of, or consist essentially of the amino acid sequence of SEQ ID NO: 40, or at least the CDRs thereof, with the aforementioned amino acid substitutions in any combination. In one embodiment, the immunoglobulin light chain polypeptide comprises, consists of, or consists essentially of an amino acid sequence of any one of SEQ ID NO: 41, SEQ ID NO: 42, SEQ ID NO: 43, or SEQ ID NO: 44; or at least the CDRs thereof.

In some embodiments, the light chain variable region comprises a LCDR1 comprising, consisting of, or consisting essentially of the amino acid sequence (a) Arg Ser Ser Lys Ser Leu Leu His Ser Asn Gly Ile Thr Tyr Phe Tyr (SEQ ID NO: 81); (b) Arg Ser Ser Lys Ser Leu Leu His Ser Asn Ala Ile Thr Tyr Phe Tyr (SEQ ID NO: 82); or (c) Arg Ser Ser Lys Ser Leu Leu His Arg Asn Ala Ile Thr Tyr Phe Tyr (SEQ ID NO: 83); a LCDR2 comprising, consisting of, or consisting essentially of the amino acid sequence Gln Met Ser Asn Leu Ala Ser (SEQ ID NO: 84); and a LCDR3 comprising, consisting of, or consisting essentially of the amino acid sequence Ala Gln Asn Leu Glu Leu Pro Leu Thr (SEQ ID NO: 85).

In further embodiments, the immunoglobulin light chain variable region comprises, consists of, or consists essentially of the amino acid sequence of Asp Ile Gln Met Thr Gln Ser Pro Ser Ser Leu Ser Ala Ser Val Gly Asp Arg Val Thr Ile Thr Cys Arg Ala Ser Gln Xaa1 Ile Asn Asn Tyr Leu Asn Trp Tyr Gln Gln Lys Pro Gly Lys Ala Pro Lys Leu Leu Ile Tyr Tyr Thr Ser Xaa2 Leu His Ser Gly Val Pro Ser Arg Phe Ser Xaa3 Ser Gly Ser Gly Xaa4 Asp Xaa5 Thr Phe Thr Ile Ser Ser Leu Gln Pro Glu Asp Ile Ala Thr Tyr Tyr Cys Gln Gln Gly His Thr Leu Pro Trp Thr Phe Gly Gly Gly Thr Lys Val Glu Ile Lys Xaa6 Xaa7 (SEQ ID NO: 58), or at least the CDRs thereof, wherein (a) Xaa1 is aspartic acid (Asp) or tryptophan (Trp), (b) Xaa2 is arginine (Arg) or methionine (Met), (c) Xaa3 is glycine (Gly), serine (Ser) or proline (Pro), (d) Xaa4 is threonine (Thr) or asparagines (Asn), (e) Xaa5 is phenylalanine (Phe) or tyrosine (Tyr), (f) Xaa6 is arginine (Arg) or absent, and (g) Xaa7 is threonine (Thr) or absent. In some embodiments, the immunoglobulin light chain variable region comprises, consists of, or consists essentially of the amino acid sequence Asp Ile Gln Met Thr Gln Ser Pro Ser Ser Leu Ser Ala Ser Val Gly Asp Arg Val Thr Ile Thr Cys Arg Ala Ser Gln Asp Ile Asn Asn Tyr Leu Asn Trp Tyr Gln Gln Lys Pro Gly Lys Ala Pro Lys Leu Leu Ile Tyr Tyr Thr Ser Arg Leu His Ser Gly Val Pro Ser Arg Phe Ser Xaa1 Ser Gly Ser Gly Thr Asp Xaa2 Thr Phe Thr Ile Ser Ser Leu Gln Pro Glu Asp Ile Ala Thr Tyr Tyr Cys Gln Gln Gly His Thr Leu Pro Trp Thr Phe Gly Gly Gly Thr Lys Val Glu Ile Lys (SEQ ID NO: 45), or at least the CDRs thereof, wherein (a) Xaa1 is serine (Ser) or proline (Pro), and (b) Xaa2 is phenylalanine (Phe) or tyrosine (Tyr).

The light chain variable region can comprise, consist of, or consist essentially of the amino acid sequence of SEQ ID NO: 58 or SEQ ID NO: 45, or at least the CDRs thereof, with one or more of the aforementioned amino acid substitutions in any suitable combination. In one embodiment, the immunoglobulin light chain polypeptide comprises, consists of, or consists essentially of an amino acid sequence of any one of SEQ ID NO: 46, SEQ ID NO: 47, or SEQ ID NO: 55, or at least the CDRs thereof.

In some embodiments, the light chain variable region comprises an LCDR1 comprising, consisting of, or consisting essentially of the amino acid sequence (a) Arg Ala Ser Gln Asp Ile Asn Asn Tyr Leu Asn (SEQ ID NO: 86); or (b) Arg Ala Ser Gln Trp Ile Asn Asn Tyr Leu Asn (SEQ ID NO: 87); an LCDR2 comprising, consisting of, or consisting essentially of an amino acid sequence (a) Tyr Thr Ser Arg Leu His Ser (SEQ ID NO: 88); or (b) Tyr Thr Ser Met Leu His Ser (SEQ ID NO: 89); and an LCDR3 comprising, consisting of, or consisting essentially of the amino acid sequence Gln Gln Gly His Thr Leu Pro Trp Thr (SEQ ID NO: 90).

In another embodiment, the immunoglobulin light chain variable region comprises, consists of, or consists essentially of the amino acid sequence of SEQ ID NO: 48, SEQ ID NO: 49, or SEQ ID NO: 50, or at least the CDRs thereof.

In some embodiments, the immunoglobulin light chain variable region comprises an amino acid sequence that is at least 90% identical (e.g., at least 91%, at least 92%, at least 93%, at least 94%, at least 95%, at least 96%, at least 97%, at least 98%, at least 99%, or 100% identical) to any of the foregoing immunoglobulin light chain variable region sequences. Nucleic acid or amino acid sequence "identity" can be determined using the methods described herein.

As described above, the IL-36R binding agent can comprise an immunoglobulin heavy chain variable region and light chain variable region have any of the foregoing heavy and light chain variable region sequences, or the CDRs thereof. The CDR sequences can be the CDR sequences set forth herein or the CDR sequences as determined using any of several known methods (e.g., Kabat, Chothia, Martin (Enhanced Chothia), IGMT, or AHo).

In one embodiment, the IL-36R binding agent has an immunoglobulin heavy chain variable region comprising SEQ ID NO: 15 or SEQ ID NO: 22, or at least the CDR regions thereof; and an immunoglobulin light chain variable region comprising SEQ ID NO: 40 or SEQ ID NO: 44, or at least the CDR sequences thereof, wherein the CDRs are as determined with determined in accordance with any of the various known immunoglobulin numbering schemes, particularly in accordance with Kabat, Chothia, Martin (Enhanced Chothia), IGMT, or AHo. For example, In some embodiments, the antibody comprises a heavy chain variable region of SEQ ID NO: 22 and light chain variable region of SEQ ID NO: 44, or at least the CDRs thereof as determined by Kabat. In some embodiments, the antibody comprises a heavy chain variable region of SEQ ID NO: 22 and light chain variable region of SEQ ID NO: 44, or at least the CDRs thereof as determined by Chothia. In some embodiments, the antibody comprises a heavy chain variable region of SEQ ID NO: 22 and light chain variable region of SEQ ID NO: 44, or at least the CDRs thereof as determined by Martin. In some embodiments, the antibody comprises a heavy chain variable region of SEQ ID NO: 22 and light chain variable region of SEQ ID NO: 44, or at least the CDRs thereof as determined by IGMT. In some embodiments, the antibody comprises a heavy chain variable region of SEQ ID NO: 22 and light chain variable region of SEQ ID NO: 44, or at least the CDRs thereof as determined by AHo.

In some embodiments, the IL-36R binding agent comprises a heavy chain variable region comprising: an HCDR1 comprising, consisting of, or consisting essentially of the amino acid sequence selected from the group consisting of (a) Tyr Thr Phe Thr Asn Tyr Trp Met His (SEQ ID NO: 64); (b) Tyr Thr Phe Thr Asn Tyr Trp Met Asn (SEQ ID NO: 65); (c) Tyr Thr Phe Thr Asn Tyr Trp Met Tyr (SEQ ID NO: 66); and (d) Tyr Thr Phe Thr Asn Tyr Tyr Met Asn (SEQ ID NO: 67); an HCDR2 comprising, consisting of, or consisting essentially of the amino acid sequence selected from the group consisting of (a) Met Phe Asp Pro Ser Asn Ser Val Thr Arg Leu Asn Gln Lys Phe Lys Asp (SEQ ID NO: 68); (b) Met Phe Glu Pro Ser Asn Ala Val Thr Arg Leu Asn Gln Lys Phe Lys Asp (SEQ ID NO: 69); (c) Met Phe His Pro Ser Asn Ala Val Thr Arg Leu Asn Gln Lys Phe Lys Asp (SEQ ID NO: 70); and (d) Met Phe His Pro Thr Gly Asp Val Thr Arg Leu Asn Gln Lys Phe Lys Asp (SEQ ID NO: 71); and/or an HCDR3 comprising, consisting of, or consisting essentially of the amino acid sequence Thr Thr Ser Met Ile Ile Gly Gly Phe Ala Tyr (SEQ ID NO: 72); and comprises a light chain variable region comprising a LCDR1 comprising, consisting of, or consisting essentially of the amino acid sequence (a) Arg Ser Ser Lys Ser Leu Leu His Ser Asn Gly Ile Thr Tyr Phe Tyr (SEQ ID NO: 81); (b) Arg Ser Ser Lys Ser Leu Leu His Ser Asn Ala Ile Thr Tyr Phe Tyr (SEQ ID NO: 82); or (c) Arg Ser Ser Lys Ser Leu Leu His Arg Asn Ala Ile Thr Tyr Phe Tyr (SEQ ID NO: 83); a LCDR2 comprising, consisting of, or consisting essentially of the amino acid sequence Gln Met Ser Asn Leu Ala Ser (SEQ ID NO: 84); and a LCDR3 comprising, consisting of, or consisting essentially of the amino acid sequence Ala Gln Asn Leu Glu Leu Pro Leu Thr (SEQ ID NO: 85).

In a particular embodiment, the IL-36R binding agent comprises a heavy chain variable region comprising: an HCDR1 comprising, consisting of, or consisting essentially of the amino acid sequence selected from the group consisting of Tyr Thr Phe Thr Asn Tyr Trp Met Asn (SEQ ID NO: 65); an HCDR2 comprising, consisting of, or consisting essentially of the amino acid sequence selected from the group consisting of Met Phe His Pro Thr Gly Asp Val Thr Arg Leu Asn Gln Lys Phe Lys Asp (SEQ ID NO: 71); and/or an HCDR3 comprising, consisting of, or consisting essentially of the amino acid sequence Thr Thr Ser Met Ile Ile Gly Gly Phe Ala Tyr (SEQ ID NO: 72); and comprises a light chain variable region comprising a LCDR1 comprising, consisting of, or consisting essentially of the amino acid sequence Arg Ser Ser Lys Ser Leu Leu His Arg Asn Ala Ile Thr Tyr Phe Tyr (SEQ ID NO: 83); a LCDR2 comprising, consisting of, or consisting essentially of the amino acid sequence Gln Met Ser Asn Leu Ala Ser (SEQ ID NO: 84); and a LCDR3 comprising, consisting of, or consisting essentially of the amino acid sequence Ala Gln Asn Leu Glu Leu Pro Leu Thr (SEQ ID NO: 85).

Furthermore, the IL-36R binding agent can comprise an immunoglobulin heavy chain variable region and light chain variable region having specified percent identities to the heavy and light chain variable region sequences, such as at least 90% identical (e.g., at least 91%, at least 92%, at least 93%, at least 94%, at least 95%, at least 96%, at least 97%, at least 98%, at least 99%, or 100% identical). In some embodiments, the variance in sequence occurs outside the CDRs (as determined by any known method including Kabat, Chothia, Martin (Enhanced Chothia), IGMT, or AHo), such that the heavy and light chain sequences having the specified sequence identity to the specific sequences set forth herein retain the CDRs of such sequences. In an embodiment, the IL-36R binding agent comprises an immunoglobulin heavy chain variable region that is at least 90% identical (e.g., at least 91%, at least 92%, at least 93%, at least 94%, at least 95%, at least 96%, at least 97%, at least 98%, at least 99%, or 100% identical) to SEQ ID NO: 15 or SEQ ID NO: 22, optionally wherein the sequence retains the CDRs of SEQ ID NO: 15 or SEQ ID NO: 22; and comprises an immunoglobulin heavy chain variable region that is at least 90% identical (e.g., at least 91%, at least 92%, at least 93%, at least 94%, at least 95%, at least 96%, at least 97%, at least 98%, at least 99%, or 100% identical) to SEQ ID NO: 40 or SEQ ID NO: 44, optionally wherein the sequence retains the CDRs of SEQ ID NO: 40 or SEQ ID NO: 44; wherein the CDRs are as determined in accordance with any of the various known immunoglobulin numbering schemes, particularly in accordance with Kabat, Chothia, Martin (Enhanced Chothia), IGMT, or AHo. In a particular embodiment, the IL-36R binding agent comprises an immunoglobulin heavy chain variable region that is at least 90% identical (e.g., at least 91%, at least 92%, at least 93%, at least 94%, at least 95%, at least 96%, at least 97%, at least 98%, at least 99%, or 100% identical) to SEQ ID NO: 22, optionally wherein the sequence retains the CDRs of SEQ ID NO: 22; and comprises an immunoglobulin heavy chain variable region that is at least 90% identical (e.g., at least 91%, at least 92%, at least 93%, at least 94%, at least 95%, at least 96%, at least 97%, at least 98%, at least 99%, or 100% identical) to SEQ ID NO: 44, optionally wherein the sequence retains the CDRs of SEQ ID NO: 44; wherein the CDRs are as determined in accordance with any of the various known immunoglobulin numbering schemes, particularly in accordance with Kabat, Chothia, Martin (Enhanced Chothia), IGMT, or AHo.

Variation in sequence identity can be accomplished through addition, substitution, or deletion of one or more amino acid residues. An amino acid "replacement" or "substitution" refers to the replacement of one amino acid at a given position or residue by another amino acid at the same position or residue within a polypeptide sequence. The amino acid replacement or substitution can be conservative, semi-conservative, or non-conservative depending upon whether the substitution is by an amino acid residue that has similar properties to the residue being replaced. A functional way to define common properties between individual amino acids is to analyze the normalized frequencies of amino acid changes between corresponding proteins of homologous organisms (Schulz and Schirmer, *Principles of Protein Structure*, Springer-Verlag, New York (1979)). According to such analyses, groups of amino acids may be defined where amino acids within a group exchange preferentially with each other, and therefore resemble each other most in their impact on the overall protein structure (Schulz and Schirmer, supra).

Amino acids can be broadly grouped as "aromatic" or "aliphatic." An aromatic amino acid includes an aromatic ring. Examples of "aromatic" amino acids include histidine (H or His), phenylalanine (F or Phe), tyrosine (Y or Tyr), and tryptophan (W or Trp). Non-aromatic amino acids are broadly grouped as "aliphatic." Examples of "aliphatic" amino acids include glycine (G or Gly), alanine (A or Ala), valine (V or Val), leucine (L or Leu), isoleucine (I or Ile), methionine (M or Met), serine (S or Ser), threonine (T or Thr), cysteine (C or Cys), proline (P or Pro), glutamic acid (E or Glu), aspartic acid (A or Asp), asparagine (N or Asn), glutamine (Q or Gln), lysine (K or Lys), and arginine (R or Arg).

Aliphatic amino acids may be sub-divided into four sub-groups. The "large aliphatic non-polar sub-group" consists of valine, leucine, and isoleucine. The "aliphatic slightly-polar sub-group" consists of methionine, serine, threonine, and cysteine. The "aliphatic polar/charged sub-group" consists of glutamic acid, aspartic acid, asparagine, glutamine, lysine, and arginine. The "small-residue sub-group" consists of glycine and alanine. The group of charged/polar amino acids may be sub-divided into three sub-groups: the "positively-charged sub-group" consisting of lysine and arginine, the "negatively-charged sub-group" consisting of glutamic acid and aspartic acid, and the "polar sub-group" consisting of asparagine and glutamine.

Aromatic amino acids may be sub-divided into two sub-groups: the "nitrogen ring sub-group" consisting of histidine and tryptophan and the "phenyl sub-group" consisting of phenylalanine and tyrosine.

Examples of conservative amino acid substitutions include substitutions of amino acids within the sub-groups described above, for example, lysine for arginine and vice versa such that a positive charge may be maintained, glutamic acid for aspartic acid and vice versa such that a negative charge may be maintained, serine for threonine such that a free —OH can be maintained, and glutamine for asparagine such that a free —$NH_2$ can be maintained. "Semi-conservative mutations" include amino acid substitutions of amino acids within the same groups listed herein, but not within the same sub-group. For example, the substitution of aspartic acid for asparagine, or asparagine for lysine, involves amino acids within the same group, but different sub-groups. "Non-conservative mutations" involve amino acid substitutions between different groups, for example, lysine for tryptophan, or phenylalanine for serine, etc.

When the immunoglobulin light chain or heavy chain variable region "consists essentially of" any of the foregoing heavy or light chain variable region amino acid sequences, additional components can be included in the polypeptide that do not materially affect the polypeptide, such as those described herein. When the immunoglobulin light chain or heavy chain variable region "consists of", the polypeptide does not comprise any additional components.

The IL-36R binding agent (e.g., antibody or antibody fragment) can be a binding agent that competes with an IL-36R binding agent comprising an immunoglobulin heavy chain polypeptide or light chain polypeptide described herein for binding to IL-36R, e.g., binds to the same epitope or an overlapping epitope. Antibody competition can be assayed using routine peptide competition assays which utilize ELISA, Western blot, or immunohistochemistry methods (see, e.g., U.S. Pat. Nos. 4,828,981 and 8,568,992; and Braitbard et al., *Proteome Sci.,* 4: 12 (2006)).

The "biological activity" of an IL-36R-binding agent refers to, for example, binding affinity for a particular IL-36R epitope, neutralization or inhibition of IL-36R-binding to its receptor(s), neutralization or inhibition of IL-36R activity in vivo (e.g., $IC_{50}$), pharmacokinetics, and cross-reactivity (e.g., with non-human homologs or orthologs of the IL-36R protein, or with other proteins or tissues). In certain embodiments, the IL-36R-binding agent desirably exhibits one or more of the following biological activities: (a) inhibits the interaction between IL-36R and IL-36α, IL-36β, and/or IL-36γ, (b) inhibits intracellular signaling mediated by IL-36R, and/or (c) cross-reacts with and inhibits the activity of human and non-human primate (e.g., cynomolgus) IL-36R. Other biological properties or characteristics of an antigen-binding agent recognized in the art include, for example, avidity, selectivity, solubility, folding, immunotoxicity, expression, and formulation. The aforementioned properties or characteristics can be observed, measured, and/or assessed using standard techniques including, but not limited to, ELISA, competitive ELISA, surface plasmon resonance analysis (BIACORE™), or KINEXA™, in vitro or in vivo neutralization assays, receptor-ligand binding assays, cytokine or growth factor production and/or secretion assays, and signal transduction and immunohistochemistry assays.

The terms "inhibit" or "neutralize," as used herein with respect to the activity of the IL-36 pathway inhibitor, e.g., the IL-36R-binding agent, refer to the ability to substantially antagonize, prohibit, prevent, restrain, slow, disrupt, alter, eliminate, stop, or reverse the progression or severity of, for example, the biological activity of an IL-36 cytokine or IL-36R, or a disease or condition associated with an IL-36 cytokine or IL-36R, e.g., ichthyosis. For example, the IL-36R-binding agent preferably inhibits or neutralizes the activity of IL-36R by at least about 20%, about 30%, about 40%, about 50%, about 60%, about 70%, about 80%, about 90%, about 95%, about 100%, or a range defined by any two of the foregoing values.

The IL-36R-binding agent of the present inventive method can be a whole antibody, as described herein, or an antibody fragment. The terms "fragment of an antibody," "antibody fragment," and "functional fragment of an antibody" are used interchangeably herein to mean one or more fragments of an antibody that retain the ability to specifically bind to an antigen (see, generally, Holliger et al., *Nat. Biotech.,* 23(9): 1126-1129 (2005)). The IL-36R-binding agent can contain any IL-36R-binding antibody fragment. The antibody fragment desirably comprises, for example, one or more CDRs, the variable region (or portions thereof), the constant region (or portions thereof), or combinations thereof. Examples of antibody fragments include, but are not limited to, (i) a Fab fragment, which is a monovalent fragment consisting of the $V_L$, $V_H$, $C_L$, and $CH_1$ domains, (ii) a $F(ab')_2$ fragment, which is a bivalent fragment comprising two Fab fragments linked by a disulfide bridge at the hinge region, (iii) a Fv fragment consisting of the $V_L$ and $V_H$ domains of a single arm of an antibody, (iv) a Fab' fragment, which results from breaking the disulfide bridge of an $F(ab')_2$ fragment using mild reducing conditions, (v) a disulfide-stabilized Fv fragment (dsFv), and (vi) a domain antibody (dAb), which is an antibody single variable region domain ($V_H$ or $V_L$) polypeptide that specifically binds antigen.

When the IL-36R-binding agent is an antibody or antibody fragment, the antibody or antibody fragment can comprise a heavy chain constant region (Fc) of any suitable class. In some embodiments, the antibody or antibody fragment comprises a heavy chain constant region that is based upon wild-type IgG1, IgG2, or IgG4 antibodies, or variants thereof. It will be appreciated that each antibody class, or isotype, engages a distinct set of effector mechanisms for disposing of or neutralizing antigen once recognized. As such, in some embodiments, when the IL-36R-binding agent is an antibody or antibody fragment, it can exhibit one or more effector functions, such as participation in antibody-dependent complement-mediated lysis or antibody-dependent cellular toxicity via interactions with effector molecules and cells (e.g., activation of the complement system).

The IL-36R-binding agent also can be a single chain antibody fragment. Examples of single chain antibody fragments include, but are not limited to, (i) a single chain Fv (scFv), which is a monovalent molecule consisting of the two domains of the Fv fragment (i.e., $V_L$ and $V_H$) joined by a synthetic linker which enables the two domains to be synthesized as a single polypeptide chain (see, e.g., Bird et al., *Science,* 242: 423-426 (1988); Huston et al., *Proc. Natl. Acad. Sci. USA,* 85: 5879-5883 (1988); and Osbourn et al., *Nat. Biotechnol.,* 16: 778 (1998)) and (ii) a diabody, which is a dimer of polypeptide chains, wherein each polypeptide chain comprises a $V_H$ connected to a $V_L$ by a peptide linker that is too short to allow pairing between the $V_H$ and $V_L$ on the same polypeptide chain, thereby driving the pairing between the complementary domains on different $V_H$-$V_L$ polypeptide chains to generate a dimeric molecule having two functional antigen binding sites. Antibody fragments are known in the art and are described in more detail in, e.g., U.S. Patent Application Publication 2009/0093024 A1.

The IL-36R-binding agent also can be an intrabody or fragment thereof. An intrabody is an antibody which is expressed and which functions intracellularly. Intrabodies typically lack disulfide bonds and are capable of modulating the expression or activity of target genes through their specific binding activity. Intrabodies include single domain fragments such as isolated $V_H$ and $V_L$ domains and scFvs. An intrabody can include sub-cellular trafficking signals attached to the N or C terminus of the intrabody to allow expression at high concentrations in the sub-cellular compartments where a target protein is located. Upon interaction with a target gene, an intrabody modulates target protein function and/or achieves phenotypic/functional knockout by mechanisms such as accelerating target protein degradation and sequestering the target protein in a non-physiological sub-cellular compartment. Other mechanisms of intrabody-mediated gene inactivation can depend on the epitope to which the intrabody is directed, such as binding to the catalytic site on a target protein or to epitopes that are involved in protein-protein, protein-DNA, or protein-RNA interactions.

The IL-36R-binding agent also can be an antibody conjugate. In this respect, the IL-36R-binding agent can be a conjugate of (1) an antibody, an alternative scaffold, or fragments thereof, and (2) a protein or non-protein moiety comprising the IL-36R-binding agent. For example, the IL-36R-binding agent can be all or part of an antibody conjugated to a peptide, a fluorescent molecule, or a chemotherapeutic agent.

The IL-36R-binding agent can be, or can be obtained from, a human antibody, a non-human antibody, or a chimeric antibody. A "chimeric" antibody is an antibody or fragment thereof comprising both human and non-human regions. Preferably, the IL-36R-binding agent is a humanized antibody. A "humanized" antibody is a monoclonal antibody comprising a human antibody scaffold and at least one CDR obtained or derived from a non-human antibody. Non-human antibodies include antibodies isolated from any non-human animal, such as, for example, a rodent (e.g., a mouse or rat). A humanized antibody can comprise, one, two, or three CDRs obtained or derived from a non-human antibody. In one embodiment of the invention, CDRH3 of the IL-36R-binding agent is obtained or derived from a mouse monoclonal antibody, while the remaining variable regions and constant region of the IL-36R-binding agent are obtained or derived from a human monoclonal antibody.

A human antibody, a non-human antibody, a chimeric antibody, or a humanized antibody can be obtained by any means, including via in vitro sources (e.g., a hybridoma or a cell line producing an antibody recombinantly) and in vivo sources (e.g., rodents). Methods for generating antibodies are known in the art and are described in, for example, Köhler and Milstein, *Eur. J. Immunol.,* 5: 511-519 (1976); Harlow and Lane (eds.), *Antibodies: A Laboratory Manual*, CSH Press (1988); and Janeway et al. (eds.), *Immunobiology, 5th Ed*., Garland Publishing, New York, NY (2001)). In certain embodiments, a human antibody or a chimeric antibody can be generated using a transgenic animal (e.g., a mouse) wherein one or more endogenous immunoglobulin genes are replaced with one or more human immunoglobulin genes. Examples of transgenic mice wherein endogenous antibody genes are effectively replaced with human antibody genes include, but are not limited to, the Medarex HUMAB-MOUSE™, the Kirin TC MOUSE™, and the Kyowa Kirin KM-MOUSE™ (see, e.g., Lonberg, *Nat. Biotechnol.,* 23(9): 1117-25 (2005), and Lonberg, *Handb. Exp. Pharmacol.,* 181: 69-97 (2008)). A humanized antibody can be generated using any suitable method known in the art (see, e.g., An, Z. (ed.), *Therapeutic Monoclonal Antibodies: From Bench to Clinic*, John Wiley & Sons, Inc., Hoboken, New Jersey (2009)), including, e.g., grafting of non-human CDRs onto a human antibody scaffold (see, e.g., Kashmiri et al., *Methods,* 36(1): 25-34 (2005); and Hou et al., *J. Biochem.,* 144(1): 115-120 (2008)). In one embodiment, a humanized antibody can be produced using the methods described in, e.g., U.S. Patent Application Publication 2011/0287485 A1.

In one embodiment, a CDR (e.g., CDR1, CDR2, or CDR3) or a variable region of the immunoglobulin heavy chain polypeptide and/or the immunoglobulin light chain polypeptide described herein can be transplanted (i.e., grafted) into another molecule, such as an antibody or non-antibody polypeptide, using either protein chemistry or recombinant DNA technology. In this regard, the invention encompasses an IL-36R-binding agent comprising at least one CDR of an immunoglobulin heavy chain and/or light chain polypeptide as described herein. The IL-36R-binding agent can comprise one, two, or three CDRs of an immunoglobulin heavy chain and/or light chain variable region as described herein.

In a preferred embodiment, the IL-36R-binding agent binds an epitope of IL-36R which blocks the binding of IL-36R to any of its ligands (e.g., IL-36α, IL-36β, and IL-36γ) and inhibits IL-36R-mediated signaling. The present inventive method also encompasses an isolated or purified epitope of IL-36R which blocks the binding of IL-36R to any of its ligands in an indirect or allosteric manner.

Further provided herein is a nucleic acid encoding the IL-36R binding agent provided herein, or at least the heavy or light chain variable region thereof. In one embodiment, the nucleic acid encodes an immunoglobulin light chain variable region or full immunoglobulin light chain of the IL-36R binding agent. In another embodiment, the nucleic acid encodes an immunoglobulin heavy chain variable region or full immunoglobulin heavy chain of the IL-36R binding agent. In yet another embodiment, the nucleic acid encodes both an immunoglobulin light chain variable region or full immunoglobulin light chain, and an immunoglobulin heavy chain variable region or full immunoglobulin heavy chain, as provided herein.

The terms "nucleic acid" and "nucleic acid sequence" are intended to encompass a polymer of DNA or RNA, i.e., a polynucleotide, which can be single-stranded or double-stranded and which can contain non-natural or altered nucleotides. The terms "nucleic acid" and "polynucleotide" as used herein refer to a polymeric form of nucleotides of any length, either ribonucleotides (RNA) or deoxyribonucleotides (DNA). These terms refer to the primary structure of the molecule, and thus include double- and single-stranded DNA, and double- and single-stranded RNA. The terms include, as equivalents, analogs of either RNA or DNA made from nucleotide analogs and modified polynucleotides such as, though not limited to, methylated and/or capped polynucleotides. Nucleic acids are typically linked via phosphate bonds to form nucleic acid sequences or polynucleotides, though many other linkages are known in the art (e.g., phosphorothioates, boranophosphates, and the like).

The nucleic acid can be part of a vector. The vector can be, for example, a plasmid, episome, cosmid, viral vector (e.g., retroviral or adenoviral), or phage. Suitable vectors and methods of vector preparation are well known in the art (see, e.g., Sambrook et al., *Molecular Cloning, a Laboratory Manual, 3rd edition*, Cold Spring Harbor Press, Cold Spring Harbor, N.Y. (2001), and Ausubel et al., *Current Protocols in Molecular Biology*, Greene Publishing Associates and John Wiley & Sons, New York, N.Y. (1994)).

In addition to the nucleic acid sequence encoding the immunoglobulin heavy and/or light chains, the vector can comprise expression control sequences, such as promoters, enhancers, polyadenylation signals, transcription terminators, internal ribosome entry sites (IRES), and the like, that provide for the expression of the coding sequence in a host cell. Exemplary expression control sequences are known in the art and described in, for example, Goeddel, *Gene Expression Technology: Methods in Enzymology*, Vol. 185, Academic Press, San Diego, Calif. (1990).

A large number of promoters, including constitutive, inducible, and repressible promoters, from a variety of different sources are well known in the art. Representative sources of promoters include for example, virus, mammal, insect, plant, yeast, and bacteria, and suitable promoters from these sources are readily available, or can be made synthetically, based on sequences publicly available, for example, from depositories such as the ATCC as well as other commercial or individual sources. Promoters can be unidirectional (i.e., initiate transcription in one direction) or bi-directional (i.e., initiate transcription in either a 3' or 5' direction). Non-limiting examples of promoters include, for example, the T7 bacterial expression system, pBAD (araA) bacterial expression system, the cytomegalovirus (CMV) promoter, the SV40 promoter, the RSV promoter. Inducible promoters include, for example, the Tet system (U.S. Pat. Nos. 5,464,758 and 5,814,618), the Ecdysone inducible system (No et al., *Proc. Natl. Acad. Sci.,* 93: 3346-3351 (1996)), the T-REX™ system (Invitrogen, Carlsbad, CA), LACSWITCH™ system (Stratagene, San Diego, CA), and the Cre-ERT tamoxifen inducible recombinase system (Indra et al., *Nuc. Acid. Res.,* 27: 4324-4327 (1999); *Nuc. Acid. Res.,* 28: e99 (2000); U.S. Pat. No. 7,112,715; and Kramer & Fussenegger, *Methods Mol. Biol.,* 308: 123-144 (2005)).

The term "enhancer" as used herein, refers to a DNA sequence that increases transcription of, for example, a nucleic acid sequence to which it is operably linked. Enhancers can be located many kilobases away from the coding region of the nucleic acid sequence and can mediate the binding of regulatory factors, patterns of DNA methylation, or changes in DNA structure. A large number of enhancers from a variety of different sources are well known in the art and are available as or within cloned polynucleotides (from, e.g., depositories such as the ATCC as well as other commercial or individual sources). A number of polynucleotides comprising promoters (such as the commonly-used CMV promoter) also comprise enhancer sequences. Enhancers can be located upstream, within, or downstream of coding sequences.

The vector also can comprise a selectable marker gene. The term "selectable marker gene," as used herein, refers to a nucleic acid sequence that allow cells expressing the nucleic acid sequence to be specifically selected for or against, in the presence of a corresponding selective agent. Suitable selectable marker genes are known in the art and described in, e.g., International Patent Application Publications WO 1992/008796 and WO 1994/028143; Wigler et al., *Proc. Natl. Acad. Sci. USA,* 77: 3567-3570 (1980); O'Hare et al., *Proc. Natl. Acad. Sci. USA,* 78: 1527-1531 (1981); Mulligan & Berg, *Proc. Natl. Acad. Sci. USA,* 78: 2072-2076 (1981); Colberre-Garapin et al., *J. Mol. Biol.,* 150: 1-14 (1981); Santerre et al., *Gene,* 30: 147-156 (1984); Kent et al., *Science,* 237: 901-903 (1987); Wigler et al., *Cell,* 11: 223-232 (1977); Szybalska & Szybalski, *Proc. Natl. Acad. Sci. USA,* 48: 2026-2034 (1962); Lowy et al., *Cell,* 22: 817-823 (1980); and U.S. Pat. Nos. 5,122,464 and 5,770,359.

In some embodiments, the vector is an "episomal expression vector" or "episome," which is able to replicate in a host cell, and persists as an extrachromosomal segment of DNA within the host cell in the presence of appropriate selective pressure (see, e.g., Conese et al., *Gene Therapy,* 11: 1735-1742 (2004)). Representative commercially available episomal expression vectors include, but are not limited to, episomal plasmids that utilize Epstein Barr Nuclear Antigen 1 (EBNA1) and the Epstein Barr Virus (EBV) origin of replication (oriP). The vectors pREP4, pCEP4, pREP7, and pcDNA3.1 from Invitrogen (Carlsbad, CA) and pBK-CMV from Stratagene (La Jolla, CA) represent non-limiting examples of an episomal vector that uses T-antigen and the SV40 origin of replication in lieu of EBNA1 and oriP.

Other suitable vectors include integrating expression vectors, which may randomly integrate into the host cell's DNA, or may include a recombination site to enable the specific recombination between the expression vector and the host cell's chromosome. Such integrating expression vectors may utilize the endogenous expression control sequences of the host cell's chromosomes to effect expression of the desired protein. Examples of vectors that integrate in a site specific manner include, for example, components of the flp-in system from Invitrogen (Carlsbad, CA) (e.g., pcDNA™5/FRT), or the cre-lox system, such as can be found in the pExchange-6 Core Vectors from Stratagene (La Jolla, CA). Examples of vectors that randomly integrate into host cell chromosomes include, for example, pcDNA3.3 (when introduced in the absence of T-antigen) from ThermoFisher (Carlsbad, CA), UCOE from Millipore (Billerica, MA), and pCI or pFN10A (ACT) FLEXI™ from Promega (Madison, WI).

Viral vectors also can be used. Representative commercially available viral expression vectors include, but are not limited to, the adenovirus-based Per.C6 system available from Crucell, Inc. (Leiden, The Netherlands), the lentiviral-based pLP1 from ThermoFisher (Carlsbad, CA), and the retroviral vectors pFB-ERV plus pCFB-EGSH from Agilent (Stratagene, La Jolla, CA).

Nucleic acid sequences encoding the inventive amino acid sequences can be provided to a cell on the same vector (i.e., in cis). A unidirectional promoter can be used to control expression of each nucleic acid sequence. In another embodiment, a combination of bidirectional and unidirectional promoters can be used to control expression of multiple nucleic acid sequences. Nucleic acid sequences encoding the inventive amino acid sequences alternatively can be provided to the population of cells on separate vectors (i.e., in trans). Each of the nucleic acid sequences in each of the separate vectors can comprise the same or different expression control sequences. The separate vectors can be provided to cells simultaneously.

The vector(s) comprising the nucleic acid(s) encoding the inventive amino acid sequences can be introduced into a host cell that is capable of expressing the polypeptides encoded thereby, including any suitable prokaryotic or eukaryotic cell. As such, the invention provides an in vitro cell or cell line comprising the inventive vector. The invention also provides an in vitro cell or cell line that expresses the immunoglobulin heavy and/or light chain polypeptides, or expresses the IL-36R binding agent. Preferred host cells are those that can be easily and reliably grown, have reasonably fast growth rates, have well characterized expression systems, and can be transformed or transfected easily and efficiently.

Examples of suitable prokaryotic cells include, but are not limited to, cells from the genera *Bacillus* (such as *Bacillus subtilis* and *Bacillus brevis*), *Escherichia* (such as *E. coli*), *Pseudomonas, Streptomyces, Salmonella*, and *Erwinia*. Particularly useful prokaryotic cells include the various strains of *Escherichia coli* (e.g., K12, HB101 (ATCC No. 33694), DH5α, DH10, MC1061 (ATCC No. 53338), and CC102).

In some embodiments, the vector is introduced into a eukaryotic cell. Suitable eukaryotic cells are known in the art and include, for example, yeast cells, insect cells, and mammalian cells. Examples of suitable yeast cells include those from the genera *Kluyveromyces, Pichia, Rhino-sporidium, Saccharomyces*, and *Schizosaccharomyces*. Preferred yeast cells include, for example, *Saccharomyces cerivisae* and *Pichia pastoris*.

Suitable insect cells are described in, for example, Kitts et al., *Biotechniques,* 14: 810-817 (1993); Lucklow, *Curr. Opin. Biotechnol.,* 4: 564-572 (1993); and Lucklow et al., *J. Virol.,* 67: 4566-4579 (1993). Preferred insect cells include Sf-9 and HI5 (Invitrogen, Carlsbad, CA).

In some embodiments, mammalian cells are utilized in the invention. A number of suitable mammalian host cells are known in the art, and many are available from the American Type Culture Collection (ATCC, Manassas, VA). Examples of suitable mammalian cells include, but are not limited to, Chinese hamster ovary cells (CHO) (e.g., ATCC No. CCL61), CHO DHFR-cells (e.g., Urlaub et al., *Proc. Natl. Acad. Sci. USA,* 97: 4216-4220 (1980)), human embryonic kidney (HEK) 293 or 293T cells (e.g., ATCC No. CRL1573), and 3T3 cells (e.g., ATCC No. CCL92). Other suitable mammalian cell lines are the monkey COS-1 (e.g., ATCC No. CRL1650) and COS-7 cell lines (e.g., ATCC No. CRL1651), as well as the CV-1 cell line (e.g., ATCC No. CCL70). Further exemplary mammalian host cells include primate cell lines and rodent cell lines, including the mouse cell line NS0 a derivative of the mouse myeloma line MOPC21 (e.g. Tysabri), and transformed cell lines. Normal diploid cells, cell strains derived from in vitro culture of primary tissue, as well as primary explants, are also suitable. Other suitable mammalian cell lines include, but are not limited to, mouse neuroblastoma N2A cells, HeLa, mouse L-929 cells, and BHK or HaK hamster cell lines, all of which are available from the ATCC. Methods for selecting suitable mammalian host cells and methods for transformation, culture, amplification, screening, and purification of cells are known in the art.

In some embodiments, the mammalian cell is a human cell. For example, the mammalian cell can be a human lymphoid or lymphoid derived cell line, such as a cell line of pre-B lymphocyte origin. Examples of human lymphoid cells lines include, without limitation, RAMOS (e.g., CRL-1596), Daudi (e.g., CCL-213), EB-3 (e.g., CCL-85), Raji cells (e.g., CCL-86), and derivatives thereof.

A nucleic acid sequence encoding the inventive amino acid sequence may be introduced into a cell by any suitable technique, such as by "transfection," "transformation," or "transduction." "Transfection," "transformation," or "transduction," as used herein, refer to the introduction of one or more exogenous polynucleotides into a host cell by using physical or chemical methods. Many transfection techniques are known in the art and include, for example, calcium phosphate DNA co-precipitation (see, e.g., Murray E. J. (ed.), *Methods in Molecular Biology, Vol. 7, Gene Transfer and Expression Protocols*, Humana Press (1991)); DEAE-dextran; electroporation; cationic liposome-mediated transfection; tungsten particle-facilitated microparticle bombardment (Johnston, *Nature,* 346: 776-777 (1990)); and strontium phosphate DNA co-precipitation (Brash et al., *Mol. Cell Biol.,* 7: 2031-2034 (1987)). Phage or viral vectors can be introduced into host cells, after growth of infectious particles in suitable packaging cells, many of which are commercially available.

The nucleic acids and cells can be used for any purpose, such as for the manufacture of the IL-36R binding agent described herein. In this respect, the invention provides a method of preparing the IL-36R binding agent comprising culturing a cell comprising a nucleic acid encoding the heavy and/or light immunoglobulin polypeptides of the IL-36R binding agent. Phrased differently, the method comprises expressing a nucleic acid encoding the immunoglobulin heavy and/or light chains of the IL-36R binding agent in a cell. It will be appreciated that the immunoglobulin heavy and light chains can be expressed from a single nucleic acid in a given cell, or the immunoglobulin heavy and light chains can be expressed from separate nucleic acids in the same cells. The method can further comprise harvesting and/or purifying the IL-36R binding agent from the cell or cell culture media using known techniques.

The invention further encompasses a composition comprising an effective amount of the IL-36 pathway inhibitor (e.g., IL-36R-binding agent), or nucleic acid sequence encoding same and a pharmaceutically acceptable (e.g., physiologically acceptable) carrier. The choice of carrier will be determined, in part, by the particular site to which the composition may be administered and the particular method used to administer the composition. The composition optionally can be sterile. The composition can be frozen or lyophilized for storage and reconstituted in a suitable sterile carrier prior to use. The compositions can be generated in accordance with conventional techniques described in, e.g.,

*Remington: The Science and Practice of Pharmacy*, 21*st Edition*, Lippincott Williams & Wilkins, Philadelphia, PA (2001).

The following examples further illustrate the invention but, of course, should not be construed as in any way limiting its scope. The composition can be used for any of the foregoing methods described herein.

Example 1

This example demonstrates that patients afflicted with ichthyosis exhibit increased gene and protein expression of IL-36 cytokines and IL-36R in skin.

Skin biopsies were taken from 60 patients of all ages having at least 15 different genotypes underlying the orphan forms of ichthyoses (e.g., congenital ichthyosiform erythroderma, lamellar ichthyosis, epidermolytic ichthyosis, Netherton syndrome, and ichthyosis with confetti), as well as from aged-matched controls (batching ages 0-<6 years, 6-<12, 12-<18, and adults). Buccal swabs or saliva sampling of the patients were collected to confirm the genotype, and thus, the proper subtype of ichthyosis, if unknown.

Biopsies were performed from the upper arm for gene expression analyses extraction. Blood was drawn for serum proteomic analysis using the OLINK proseek proteomic platform, allowing for detection of close to 300 inflammatory biomarkers in serum.

Gene expression from RNAseq experiments was preprocessed using Harshlight for quality control, GCRMA algorithm for normalization, and GC-content background correction. Log 2 transformed expression values for microarrays were modeled with mixed-effects linear model with severity as fixed factors and patients as random effects, which allowed accounting for the within-patient correlation structure. Hypothesis testing for the comparisons of interest were carried for specified contrasts using the R limma's framework. P-values were adjusted for multiplicity using Benjamini and Hochberg approach. FCH>2 and FDR<0.05 were used as cut-offs to identify differentially expressed genes (DEGs). Downstream analysis included Ingenuity Pathway Analysis (IPA) and extensive use of bioinformatics tools that provided biological insights. Gene Set Enrichment Analysis (GSEA) and Gene Set Variation Analysis (GSVA) were used for obtaining enrichment scores for AD related pathways.

Figure 1B:
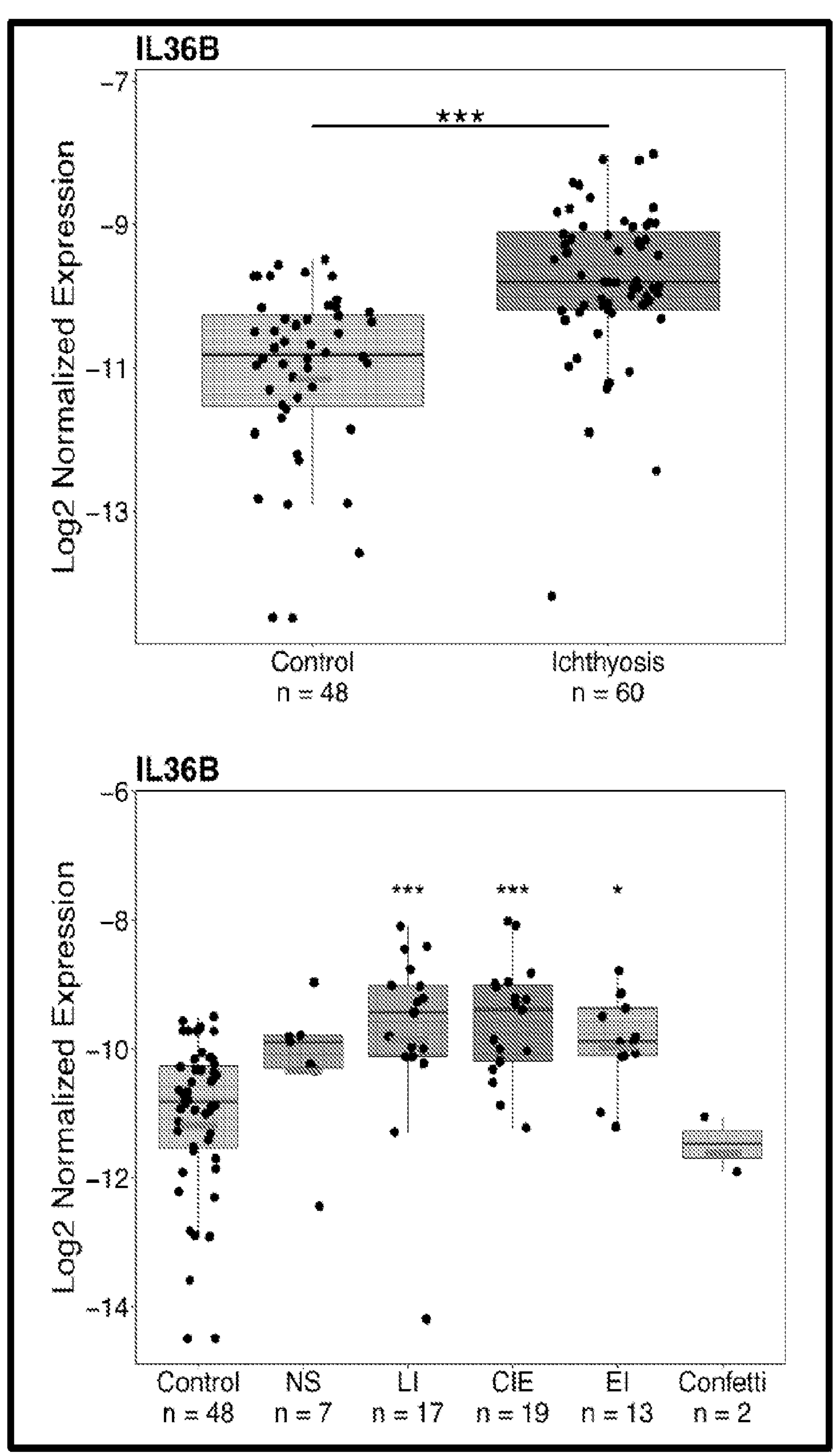
FIG. 1B shows two bar graphs depicting gene expression of IL-36β in skin biopsies patients with ichthyosis (i.e., Netherton syndrome, lamellar ichthyosis, congenital ichthyosiform erythroderma, epidermolytic ichthyosis, and ichthyosis with confetti) as compared to control.
Figure 1C:
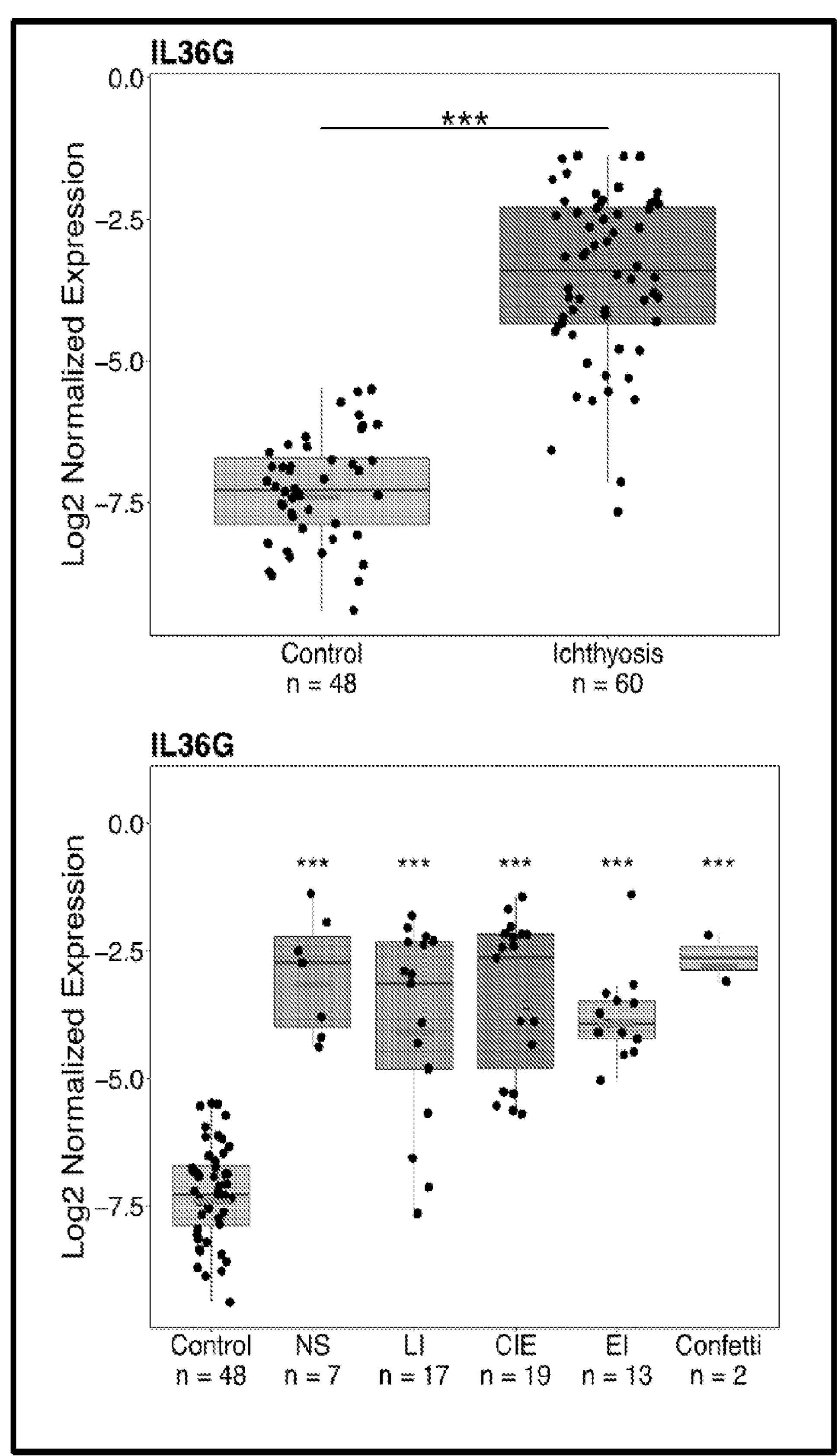
FIG. 1C shows two bar graphs depicting gene expression of IL-36γ in skin biopsies of patients with ichthyosis (i.e., Netherton syndrome, lamellar ichthyosis, congenital ichthyosiform erythroderma, epidermolytic ichthyosis, and ichthyosis with confetti) as compared to control.
Figure 1D:
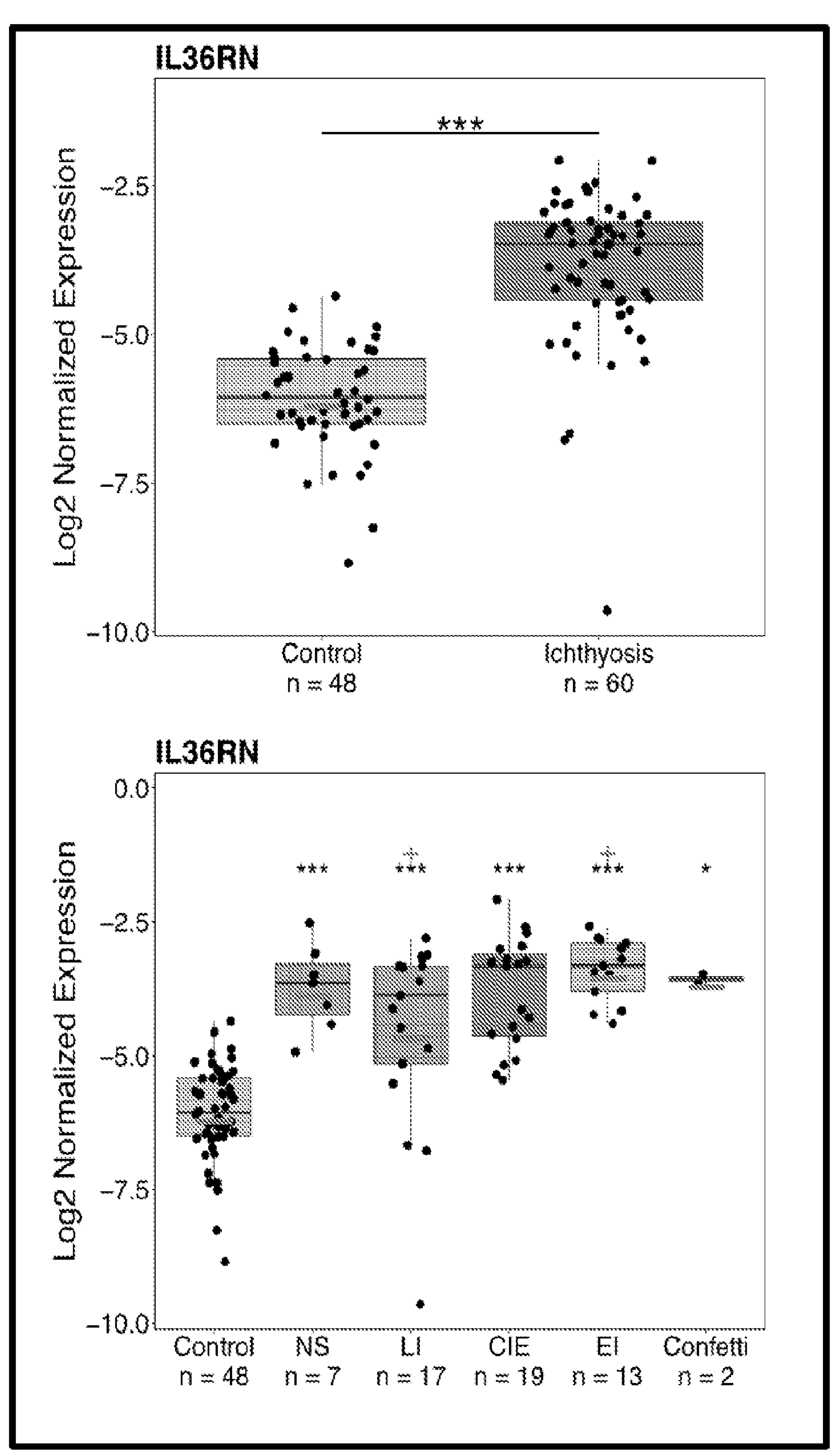
FIG. 1D shows two bar graphs depicting gene expression of IL-RN in skin biopsies of patients with ichthyosis (i.e., Netherton syndrome, lamellar ichthyosis, congenital ichthyosiform erythroderma, epidermolytic ichthyosis, and ichthyosis with confetti) as compared to control.
Figure 2A:
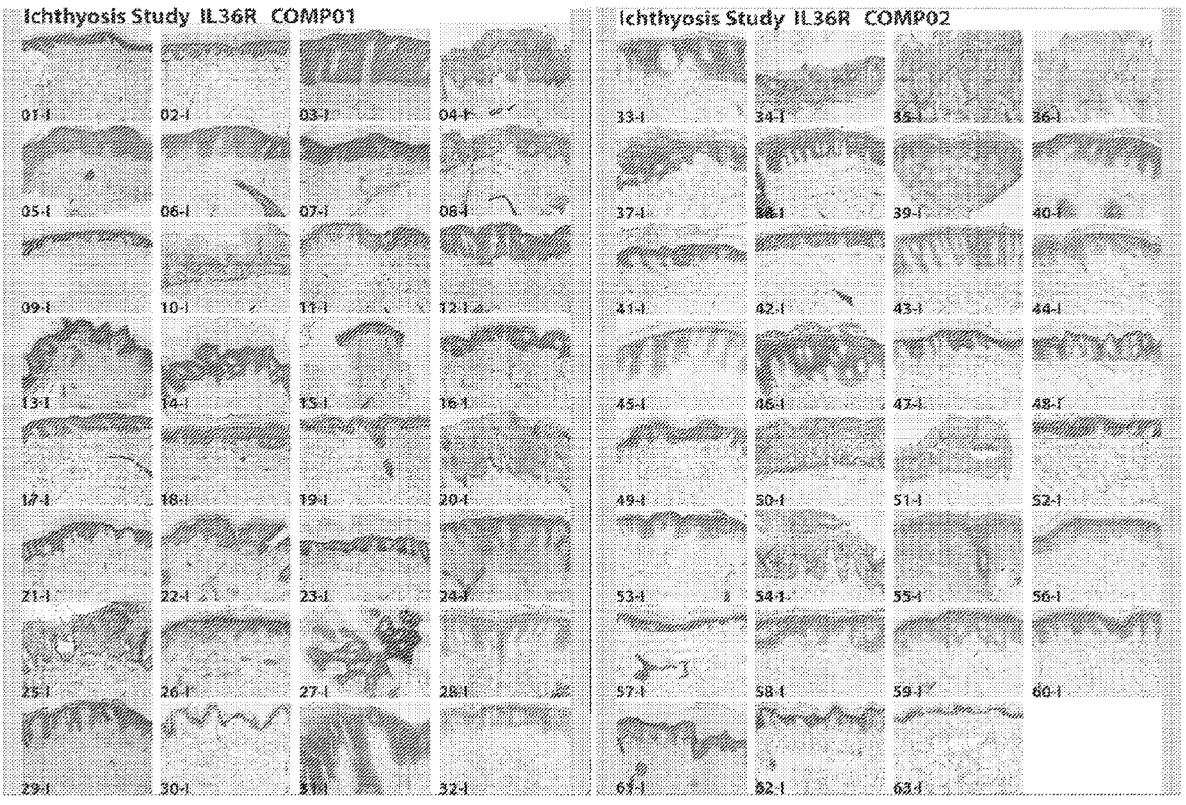
FIG. 2A shows protein expression of IL-36R in skin biopsies of patients with ichthyosis using immunohistochemistry (IHC).
Figure 2B:
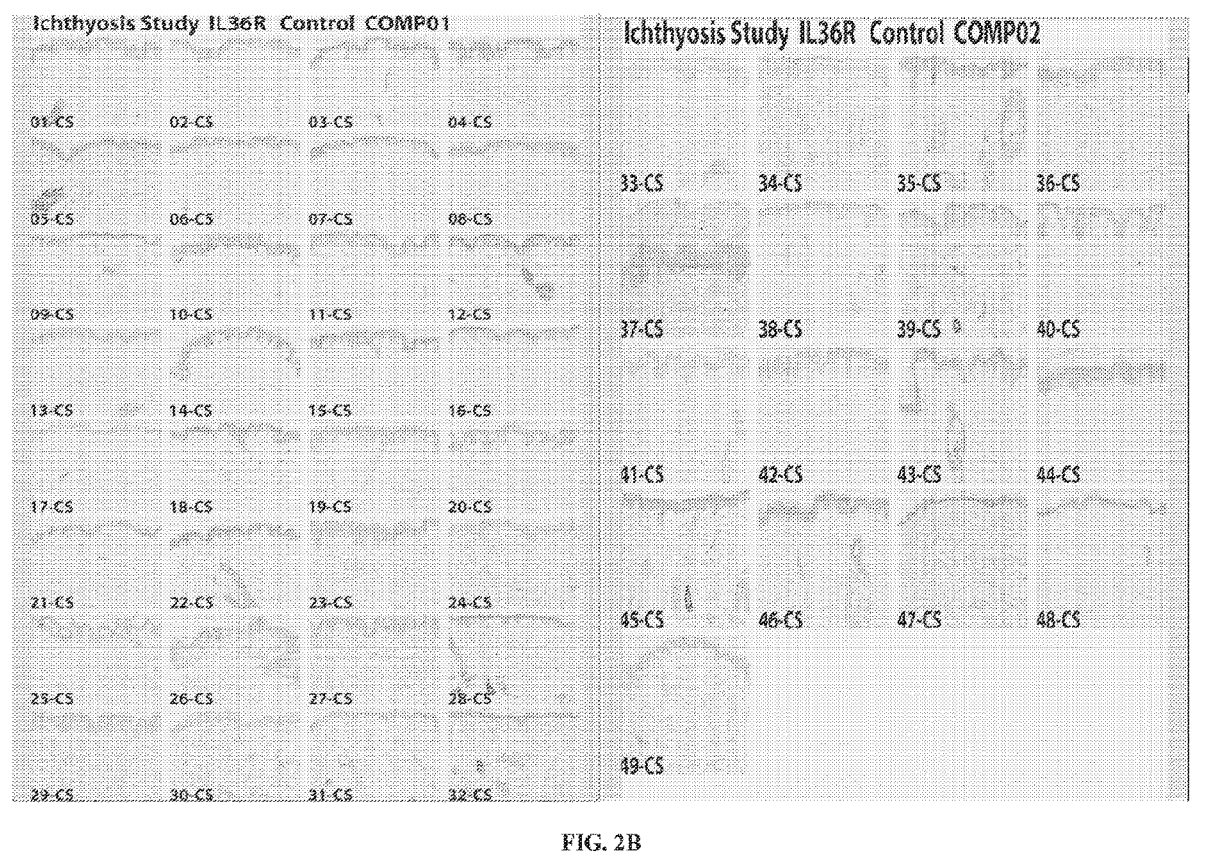

As evidenced by FIGS. 1A-D and FIGS. 2A and 2B, patients with ichthyosis exhibited significantly higher levels of gene and protein expression of the IL-36 cytokines and IL-36R as compared to control.

Example 2

This Example illustrates the effect of an IL-36R binding agent (e.g., an anti-IL-36R antibody) on ichthyosis.

Male and female adolescent and adult subjects with clinically confirmed diagnosis of ichthyosis are selected for treatment with either placebo or IL-36R binding agent. Subjects can have a diagnosis of ichthyosis subtype confirmed by genetic testing and have as of Day 1: an Ichthyosis Area Severity Index (IASI) total score of at least 18, erythema score of at least 2 (moderate severity) in at least 1 body region and scaling score of at least 2 (moderate severity) in at least 1 body region as evaluated by IASI, and BSI involved with ichthyosis of at least 50%.

The subjects can be randomized (e.g., 2:1) to receive either IL-36R binding agent (e.g., an antibody comprising heavy chain variable region SEQ ID NO: 22, light chain variable region SEQ ID NO: 44, or at least the CDRs thereof) or placebo, subcutaneously administered. The administration can be, for instance, on 4 occasions. For example, on Day 1, subjects are given a 400 mg dose of IL-36R binding agent or placebo. On Days 29, 57, and 85, the subjects are given a 200 mg dose of IL-36R binding agent or placebo.

Disease activity can be evaluated using the IASI, IASI erythema (IASI-E) subscore, IASI scaling (IASI-S) subscore, Netherton Area and Severity Assessment (NASA) for subjects with Netherton Syndrome only, Investigator Global Assessment (IGA), and body surface area (BSA) involved with ichthyosis. Quality of life can be evaluated using Ichthyosis Quality of Life—32 items (iQoL-32) in subjects ≥15 years of age only, Dermatology Life Quality Index (DLQI) for subjects ≥16 years of age, and Children's Dermatology Life Quality Index (CDLQI) for subjects less than 16 years of age. Subjects are also evaluated for disease-associated characteristics, such as worst and average pruritus and pain using an Numeric Rating Scale (NRS), impression of severity using the Patient Global Impression of Severity (PGI-S) and impression of change using the Patient Global Impression of Change (PGI-C), as well as changes in transepidermal water loss (TEWL).

Administration of the IL-36R binding agent treats ichthyosis by reducing disease activity, improving quality of life, and/or reducing disease-associated characteristics in the subjects as compared to the administration of the placebo.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of treating ichthyosis in a subject, the method comprising administering to the subject an IL-36R-binding agent that comprises a heavy chain comprising:

a HCDR1 of SEQ ID NO: 65, a HCDR2 of SEQ ID NO: 71, and HCDR3 of SEQ ID No: 72;

and a light chain polypeptide comprising:

or at least a LCDR1 of SEQ ID NO: 83, LCDR2 of SEQ ID NO: 84, and LCDR3 of SEQ ID NO: 85.

2. The method of claim 1, wherein the ichthyosis is congenital ichthyosiform erythroderma, lamellar ichthyosis, epidermolytic ichthyosis, Netherton syndrome, or ichthyosis with confetti.

3. The method of claim 1, wherein the subject is a mammal.

4. The method of claim 1, wherein the mammal is a human.

5. The method of claim 1, wherein the subject has increased skin expression of at least one of an interleukin-36 (IL-36) cytokine, interleukin-36 receptor (IL-36R), or mRNA encoding same.

6. The method of claim 5, wherein the IL-36 cytokine is IL-36α, IL-36β, or IL-36γ.

7. The method of claim 1, wherein the immunoglobulin heavy chain polypeptide of the IL-36R-binding agent comprises SEQ ID NO: 22 or at least the CDRs thereof.

8. The method of claim 1, wherein the immunoglobulin light chain polypeptide of the IL-36-binding agent comprises SEQ ID NO: 44 or at least the CDRs thereof.

9. The method of claim 1, wherein the IL-36R-binding agent exhibits one or more of the following biological activities:

(a) inhibits the interaction between IL-36R and IL-36α, IL-36β, and/or IL-36γ, (b) inhibits intracellular signaling mediated by IL-36R, (c) cross-reacts with and inhibits the activity of human IL-36R, cynomolgus IL-36R, and non-human primate IL-36R.

10. The method of claim 1, wherein the IL-36R-binding agent is an antibody, an antibody conjugate, or an antigen-binding fragment thereof.

11. The method of claim 10, wherein the IL-36R-binding agent is a $F(ab')_2$ fragment, a Fab' fragment, a Fab fragment, a Fv fragment, a scFv fragment, a dsFv fragment, a dAb fragment, or a single-chain binding polypeptide.

12. The method of claim 1, wherein the method comprises administering the IL-36R-binding agent with a pharmaceutically acceptable carrier.

13. The method of claim 1, wherein the half-life of the IL-36R-binding agent in the mammal after administration is between 30 minutes and 45 days.

14. The method of claim 1, wherein the IL-36R-binding agent binds to IL-36R with a KD between about 1 picomolar (pM) and about 100 micromolar (μM).

* * * * *